(12) United States Patent
Agata

(10) Patent No.: US 9,939,212 B2
(45) Date of Patent: Apr. 10, 2018

(54) METHOD FOR IMPROVING FLUID FLOW CHARACTERISTICS, HEAT EXCHANGER, DISTILLATION APPARATUS AND DEODORIZING APPARATUS WITH THE SAME APPLIED THERETO, AND EXPANDED METAL USED FOR THE SAME

(71) Applicant: Takahiro Agata, Osaka (JP)

(72) Inventor: Takahiro Agata, Osaka (JP)

( * ) Notice: Subject to any disclaimer, the term of this patent is extended or adjusted under 35 U.S.C. 154(b) by 67 days.

(21) Appl. No.: 14/901,906

(22) PCT Filed: Oct. 15, 2013

(86) PCT No.: PCT/JP2013/077904
§ 371 (c)(1),
(2) Date: Dec. 29, 2015

(87) PCT Pub. No.: WO2015/056290
PCT Pub. Date: Apr. 23, 2015

(65) Prior Publication Data
US 2016/0370128 A1 Dec. 22, 2016

(51) Int. Cl.
*F28F 13/12* (2006.01)
*F28F 3/02* (2006.01)
(Continued)

(52) U.S. Cl.
CPC .............. *F28F 3/027* (2013.01); *A61L 9/00* (2013.01); *B01D 3/008* (2013.01); *F28D 9/0075* (2013.01);
(Continued)

(58) Field of Classification Search
CPC .... F28F 1/128; F28F 3/27; F28F 3/083; F28F 13/02; F28F 13/12; F28D 1/05383;
(Continued)

(56) References Cited

U.S. PATENT DOCUMENTS 3,981,356 A 9/1976 Granetzke
5,282,507 A 2/1994 Tongu et al.
(Continued)

FOREIGN PATENT DOCUMENTS

JP 61-271017 12/1986
JP 5-69568 9/1993
(Continued)

OTHER PUBLICATIONS

International Search Report dated Jan. 21, 2014 in International (PCT) Application No. PCT/JP2013/077904.

*Primary Examiner* — Davis Hwu
(74) *Attorney, Agent, or Firm* — Wenderoth, Lind & Ponack, L.L.P.

(57) ABSTRACT

A channel forming body for mounting semiconductor power modules or a heat sink for power modules has a heat-transfer portion having a very complicated construction in order to increase the heat-transfer coefficient, leading to need for extremely high techniques and high cost for manufacturing. By arranging an expanded metal 13 in a channel 12 formed to lie between two planes 11 and 11 placed face-to-face, local fluid flows 16 guided by the expanded metal 13 are allowed to act on various boundary layers 15 formed between these two planes 11 and 11 and a fluid so as to improve fluid flow characteristics concerning heat transfer and/or mass transfer through a local turbulent flow acceleration effect.

6 Claims, 27 Drawing Sheets

(51) Int. Cl.
  *F28F 3/08*       (2006.01)
  *F28F 9/00*       (2006.01)
  *F28D 9/00*       (2006.01)
  *F28D 9/02*       (2006.01)
  *A61L 9/00*       (2006.01)
  *B01D 3/00*       (2006.01)
  *F28F 13/02*      (2006.01)
  *H01L 23/373*     (2006.01)
  *H01L 23/473*     (2006.01)
  *F28D 21/00*      (2006.01)

(52) U.S. Cl.
  CPC ............. *F28D 9/02* (2013.01); *F28F 3/083* (2013.01); *F28F 9/001* (2013.01); *F28F 13/02* (2013.01); *F28F 13/12* (2013.01); *H01L 23/3733* (2013.01); *H01L 23/473* (2013.01); *F28D 2021/0061* (2013.01); *F28F 2215/08* (2013.01); *F28F 2255/12* (2013.01)

(58) Field of Classification Search
  CPC .. F28D 9/0075; F28D 9/02; F28D 2021/0061; H01L 23/3733; H01L 23/473; A61L 9/00; B01D 3/008

USPC ...................................................... 165/109.1
  See application file for complete search history.

(56) References Cited

U.S. PATENT DOCUMENTS

| | | | |
|---|---|---|---|
| 5,730,213 A * | 3/1998 | Kiser | F28D 1/05383 |
| | | | 165/109.1 |
| 8,034,510 B2 | 10/2011 | Moteki et al. | |
| 2008/0047696 A1* | 2/2008 | Sperandei | F28F 1/128 |
| | | | 165/109.1 |
| 2009/0239120 A1 | 9/2009 | Moteki | |
| 2010/0096117 A1 | 4/2010 | Seido et al. | |

FOREIGN PATENT DOCUMENTS

| | | |
|---|---|---|
| JP | 2008-108573 | 5/2008 |
| JP | 2010-115705 | 5/2010 |
| JP | 2011-177004 | 9/2011 |
| JP | 2012-033966 | 2/2012 |
| WO | 2008/018429 | 2/2008 |

* cited by examiner

[Type II]

[Type I]

LW: Long way of mesh
SW: Short way of mesh
T: Thickness
W: Width
D: Whole thickness of expanded metal
Strand: Thin portion of mesh
Bond: Thick portion of intersection of meshes (1)

(2)

(3)

(1)

LW=30.5 [mm]
SW=12.0 [mm]
T=1.5 [mm]
W=1.7 [mm]
D=3.3 [mm]

(2)

LW=15.0 [mm]
SW=6.0 [mm]
T=0.7 [mm]
W=2.1 [mm]
D=3.5 [mm]

(3)

LW=15.0 [mm]
SW=6.0 [mm]
T=0.3 [mm]
W=2.1 [mm]
D=3.2 [mm]

Expanded metal (a)

LW=30.5 [mm]
SW=12.0 [mm]
T=1.5 [mm]
W=1.7 [mm]
D=3.3 [mm]

Expanded metal (b)

LW=14.0 [mm]
SW=7.0 [mm]
T=0.8 [mm]
W=1.0 [mm]
D=1.5 [mm]

(1)
Heat exchanger tube internal diameter
d=14mm

Cooling water 200 [ml/s]
Cooling water 200 [ml/s]
Cooling water 200 [ml/s]

(2)

a = 73mm
b = 5.4mm
Equivalent diameter de = 10mm

Cooling water 600 [ml/s]

(3)

LW=20mm, SW=10mm
T=0.5mm, W=3.54mm
D=5.4mm

Cooling water 600 [ml/s]

METHOD FOR IMPROVING FLUID FLOW CHARACTERISTICS, HEAT EXCHANGER, DISTILLATION APPARATUS AND DEODORIZING APPARATUS WITH THE SAME APPLIED THERETO, AND EXPANDED METAL USED FOR THE SAME

TECHNICAL FIELD

The present invention relates to a method for improving fluid flow characteristics, a heat exchanger (condenser, absorber, regenerator and the like), a distillation apparatus and a deodorizing apparatus with said improving method applied thereto, and an expanded metal used for the improving method, and more particularly, to a method for improving fluid flow characteristics whereby the flow characteristics of a fluid running in a channel lying between two planes are greatly improved with an extremely simple construction, a heat exchanger, a distillation apparatus and a deodorizing apparatus, the heat-transfer efficiency and the mass-transfer efficiency of which are substantially enhanced by applying said improving method thereto, and an expanded metal used for the improving method.

BACKGROUND ART

The flows of fluids running in channels are classified into two kinds. One is a single-phase flow in which a gas or a liquid flows in a single phase, and the other is a gas-liquid two-phase flow in which a gas and a liquid are mixed to flow.

As a device including the single-phase flow, a heat exchanger for heating or cooling is exemplified. Improvements for reducing the thermal resistance between a heat source and a fluid have been continued.

In recent years, with increasing calorific values and sizes of semiconductor power modules which are incorporated into power converters in electric vehicles, hybrid cars, large wind power generators, railway vehicles or the like, a cooling device as a heat exchanger having a higher cooling power has been required.

As regards that, an invention related to a form of a radiation fin for directly cooling with a liquid current (see Patent Document 1), an invention wherein a cooling medium circulating between standing walls of a comb teeth member is caused to circle by a plurality of guides so as to make an uneven temperature distribution of the cooling medium difficult to occur in the cooling medium channel (see Patent Document 2), or the like has been proposed.

As devices including the gas-liquid two-phase flow, an evaporator, an absorber, a regenerator and a condenser of a lithium bromide system (LiBr) absorption refrigerating machine are exemplified.

The lithium bromide system absorption refrigerating machine comprises an evaporator, an absorber, a regenerator and a condenser. Among these four heat exchangers, three heat exchangers except the regenerator are of a shell & tube type wherein heat exchanger tubes are horizontally disposed within a shell. Water is allowed to flow in the heat exchanger tubes which function as heating tubes or cooling tubes. By devising how to arrange a group of heat exchanger tubes, how many heat exchanger tubes are used and the like, the powers thereof are enhanced.

In the absorber, a liquid film of a lithium bromide solution flowing down on the surface of a cooling tube absorbs steam vaporized in the evaporator, and in the system wherein the absorber and the evaporator communicate with each other, a high vacuum is maintained. When the lithium bromide solution absorbs steam, heat of absorption is generated, and therefore, by cooling water running in the cooling tube, the lithium bromide solution is allowed to cool.

In the condenser, steam generated in the regenerator is turned back into water (a liquid) by condensation on the surface of the cooling tube, which is sent to the evaporator.

As another device including the gas-liquid two-phase flow, a distillation apparatus is exemplified.

The distillation apparatus is aimed at separating a low-boiling component and a high-boiling component. Usually a distillation column is installed on a reboiler, and a condenser is arranged near the column top.

Steam generated by heating in the reboiler moves from the column bottom in the column up to the condenser, in which it is cooled, resulting in a condensate. Part of the condensate is distilled, while the rest thereof is refluxed to the column top. The reflux liquid flowing down and the steam moving upward make countercurrent contact. Since the steam moving upward has large enthalpy, it gives heat to the reflux liquid flowing down so as to vaporize part of the reflux liquid.

At that time, since steam richer in low-boiling component compared with the composition of the reflux liquid is generated, a rectification effect is caused. Since the steam gives heat to the reflux liquid, the temperature abruptly decreases in the neighborhood of the contact surface with the reflux liquid and part of the steam in the vicinity thereof is condensed. Since the condensed part thereof is richer in high-boiling component compared with the main part of the steam, another rectification effect is caused. By accumulating such rectification effects in multiple stages in the direction of the column axis, the low-boiling component and the high-boiling component are separated. As a result, the low-boiling component is condensed in the column top portion, while the high-boiling component is condensed in the column bottom portion (the source of the above explanation of the principle of a distillation apparatus: a thesis for a doctorate in Graduate School of Engineering, Nagoya University, "The development of a technique for analyzing separation performance of a packed water distillation column for hydrogen isotope separation", Takahiko Sugiyama).

As for the distillation apparatus, a plate column and a packed column, wherein the gas-liquid contact area is enlarged and the turbulence of each phase of the gas-liquid countercurrent is increased so as to enhance the multistage rectification effects have been developed. Even a distillation column with a height of 50 m has been in the actual use.

Both a channel forming body for mounting semiconductor power modules described in the Patent Document 1 and a heat sink for power modules described in the Patent Document 2, have a heat-transfer portion having a very complicated construction in order to increase the heat-transfer coefficient. Consequently, there is a problem that extremely high techniques and a high cost are required for manufacturing them.

As heat exchanger tubes of the above shell & tube type heat exchanger in the lithium bromide system absorption refrigerating machine, high-performance and expensive heat exchanger tubes having improved forms of the inside and outside are used. However, these heat exchanger tubes usually have an overall heat-transfer coefficient of 5000 $W/m^2 \cdot K$ (tubeside area basis) or less. Therefore, there is a problem that, in order to secure a sufficient heat-transfer area, a large number of heat exchanger tubes should be effectively arranged within the shell, leading to a high cost.

In the absorber, within the liquid film of the lithium bromide solution flowing down in the heat exchanger tube, a temperature boundary layer and a density boundary layer are formed. Therefore, there is a problem that the absorption and diffusion of cooling medium steam into the liquid film of the lithium bromide solution are restricted.

In the condenser, when the condensate flows down in the form of a liquid film on the surface of the heat exchanger tube, heat transfer occurs between the surface of the liquid film and steam through convective heat transfer, while heat transfer occurs between an inner part of the liquid film and the heat-transfer surface through thermal conduction, and the condensation heat transfer coefficient depends on the thickness of the liquid film. There is a problem that the thicker the liquid film becomes, the smaller the condensation heat transfer coefficient becomes.

In the distillation column, when both fluids, a reflux liquid and steam are allowed to slowly flow in the gas-liquid countercurrent contact thereof, vaporization/condensation is sufficiently repeated, resulting in a better mass-transfer efficiency, a higher distillation effect and a smaller pressure loss. As a result, the height of the column can be reduced. However, as for the plate distillation column industrially used in actual, there are problems that the pressure loss is large, and that the height thereof is large since a construction wherein maintenance can be performed is required. On the other hand, as for the packed distillation column, there are problems that drift currents easily occur in a reflux liquid, and that it is also difficult to control the falling rate thereof.

PRIOR ART DOCUMENT

Patent Document

Patent Document 1: Japanese Patent Application Laid-Open Publication No. 2011-177004
Patent Document 2: Japanese Patent Application Laid-Open Publication No. 2012-33966

SUMMARY OF THE INVENTION

Means for Solving Problem and the Effect

As described in the above Patent Documents, both a channel forming body for mounting semiconductor power modules and a heat sink for power modules, have a heat-transfer portion having a very complicated construction in order to increase the heat-transfer coefficient. When manufacturing them, extremely high techniques and a high cost are required.

The present invention was developed in order to solve the above problems, and it is an object of the present invention to provide a method for improving fluid flow characteristics whereby the flow characteristics of a fluid running in a channel lying between two planes are greatly improved with an extremely simple construction, a heat exchanger, a distillation apparatus and a deodorizing apparatus, the heat-transfer efficiency and the mass-transfer efficiency of which are substantially enhanced by applying said improving method thereto, and furthermore, an expanded metal used for the improving method.

In order to achieve the above object, a method for improving fluid flow characteristics according to a first aspect of the present invention is characterized by arranging an expanded metal in a channel formed to lie between two planes placed face-to-face, wherein local fluid flows guided by the expanded metal are allowed to act on various boundary layers formed between these two planes and a fluid so as to improve the fluid flow characteristics concerning heat transfer and/or mass transfer through a local turbulent flow acceleration effect.

In the method for improving fluid flow characteristics according to the first aspect of the present invention, an expanded metal for improving fluid flow characteristics concerning heat transfer and/or mass transfer is arranged in a channel formed to lie between two planes placed face-to-face, and local fluid flows guided by the expanded metal are allowed to act on various boundary layers formed between these two planes and a fluid. The flow characteristics concerning heat transfer and/or mass transfer of the fluid can be greatly improved through this local turbulent flow acceleration effect. In addition, with an extremely simple construction wherein the expanded metal is just arranged in the channel formed to lie between the two planes, the fluid flow characteristics concerning heat transfer and/or mass transfer can be significantly improved. Therefore, a heat-transfer portion having a very complicated construction is not necessary, and high techniques and a high cost are not required for manufacturing, unlike the above-mentioned conventional cases. As a result, the cost can be substantially reduced.

The method for improving fluid flow characteristics according to a second aspect of the present invention is characterized by the expanded metal arranged in the channel in such a manner that the long way of an expanded metal mesh crosses the flow direction of the fluid at right angles in the method for improving fluid flow characteristics according to the first aspect of the present invention.

In the method for improving fluid flow characteristics according to the second aspect of the present invention, by further enhancing the local turbulent flow acceleration effect, significant improvements in fluid flow characteristics concerning heat transfer and/or mass transfer of the fluid can be realized more stably.

The method for improving fluid flow characteristics according to a third aspect of the present invention is characterized by making the width W of the expanded metal larger than that of a standardized article so as to increase the whole thickness D of the expanded metal in the method for improving fluid flow characteristics according to the first or second aspect of the present invention.

In the method for improving fluid flow characteristics according to the third aspect of the present invention, the circulation resistance of the fluid in the channel can be reduced, and moreover, the turbulent flow acceleration effect of the local fluid flows guided by the expanded metal can be enhanced, leading to more significant improvements in fluid flow characteristics concerning heat transfer and/or mass transfer of the fluid.

The method for improving fluid flow characteristics according to a fourth aspect of the present invention is characterized by setting the length of the hypotenuse of an isosceles right triangle having the other two sides with a length of the width W of the expanded metal to be half of the short way SW of the expanded metal mesh in the method for improving fluid flow characteristics according to the third aspect of the present invention.

In the method for improving fluid flow characteristics according to the fourth aspect of the present invention, the whole thickness of the expanded metal can be maximized. As a result, the reduction of the circulation resistance of the fluid in the channel, the enhancement of the turbulent flow acceleration effect of the local fluid flows guided by the expanded metal, and the improvement of the fluid flow characteristics concerning heat transfer and/or mass transfer of the fluid can be more significantly and certainly realized.

A heat exchanger according to the present invention is characterized by the method for improving fluid flow characteristics described in any one of the first to fourth aspects of the present invention being applied thereto.

In the heat exchanger, an expanded metal for improving fluid flow characteristics concerning heat transfer is arranged in a channel formed to lie between two planes placed face-to-face, local fluid flows guided by the expanded metal act on various boundary layers formed between these two planes and a fluid, and the fluid flow characteristics concerning heat transfer of the fluid can be significantly improved through a local turbulent flow acceleration effect. Furthermore, since the construction wherein the expanded metal is just arranged in the channel formed to lie between the two planes is extremely simple, a heat-transfer portion having a very complicated construction is not necessary, and high techniques and a high cost are not required for manufacturing, unlike the above conventional cases. As a result, the cost can be substantially reduced.

A distillation apparatus according to the present invention is characterized by the method for improving fluid flow characteristics described in any one of the first to fourth aspects of the present invention being applied thereto.

In the distillation apparatus, an expanded metal for improving fluid flow characteristics concerning heat transfer and mass transfer is arranged in a channel formed to lie between two planes placed face-to-face, local fluid flows guided by the expanded metal act on various boundary layers formed between these two planes and a fluid, and the fluid flow characteristics concerning heat transfer and mass transfer of the fluid can be significantly improved through a local turbulent flow acceleration effect. Furthermore, since the construction wherein the expanded metal is just arranged in the channel formed to lie between the two planes is extremely simple, a heat-transfer portion and a mass-transfer portion having a very complicated construction are not necessary, and high techniques and a high cost are not required for manufacturing, unlike the above conventional cases. As a result, the cost can be substantially reduced.

A deodorizing apparatus according to the present invention is characterized by the method for improving fluid flow characteristics described in any one of the first to fourth aspects of the present invention being applied thereto.

In the deodorizing apparatus, an expanded metal for improving fluid flow characteristics concerning mass transfer is arranged in a channel formed to lie between two planes placed face-to-face, local fluid flows guided by the expanded metal act on various boundary layers formed between these two planes and a fluid, and the fluid flow characteristics concerning mass transfer of the fluid can be significantly improved through a local turbulent flow acceleration effect. Furthermore, since the construction wherein the expanded metal is just arranged in the channel formed to lie between the two planes is extremely simple, a mass-transfer portion having a very complicated construction is not necessary, and high techniques and a high cost are not required for manufacturing, unlike the above conventional cases. As a result, the cost can be substantially reduced.

An expanded metal according to a first aspect of the present invention is characterized by an expanded metal used in the method for improving fluid flow characteristics according to the third aspect of the present invention, having a width W being set to be larger than that of a standardized article and a whole thickness D being set to be larger than that of the standardized article.

Using the expanded metal according to the first aspect of the present invention, the fluid circulation resistance in a channel formed to lie between two planes placed face-to-face can be reduced. Moreover, the effect of local fluid flows guided by the expanded metal can be enhanced, and the fluid flow characteristics concerning heat transfer and/or mass transfer of the fluid can be more significantly improved.

An expanded metal according to a second aspect of the present invention is characterized by an expanded metal used in the method for improving fluid flow characteristics according to the fourth aspect of the present invention, having a length of the hypotenuse of an isosceles right triangle having the other two sides with a length of the width W set to be half of the short way SW of the mesh.

As for the expanded metal according to the second aspect of the invention, the whole thickness of the expanded metal becomes the largest. As a result, the reduction of the fluid circulation resistance in a channel formed to lie between two planes placed face-to-face, the enhancement of the effect of local fluid flows guided by the expanded metal, and the improvement of the fluid flow characteristics concerning heat transfer and/or mass transfer of the fluid can be more significantly and certainly realized.

MODE FOR CARRYING OUT THE INVENTION

Figure 1:
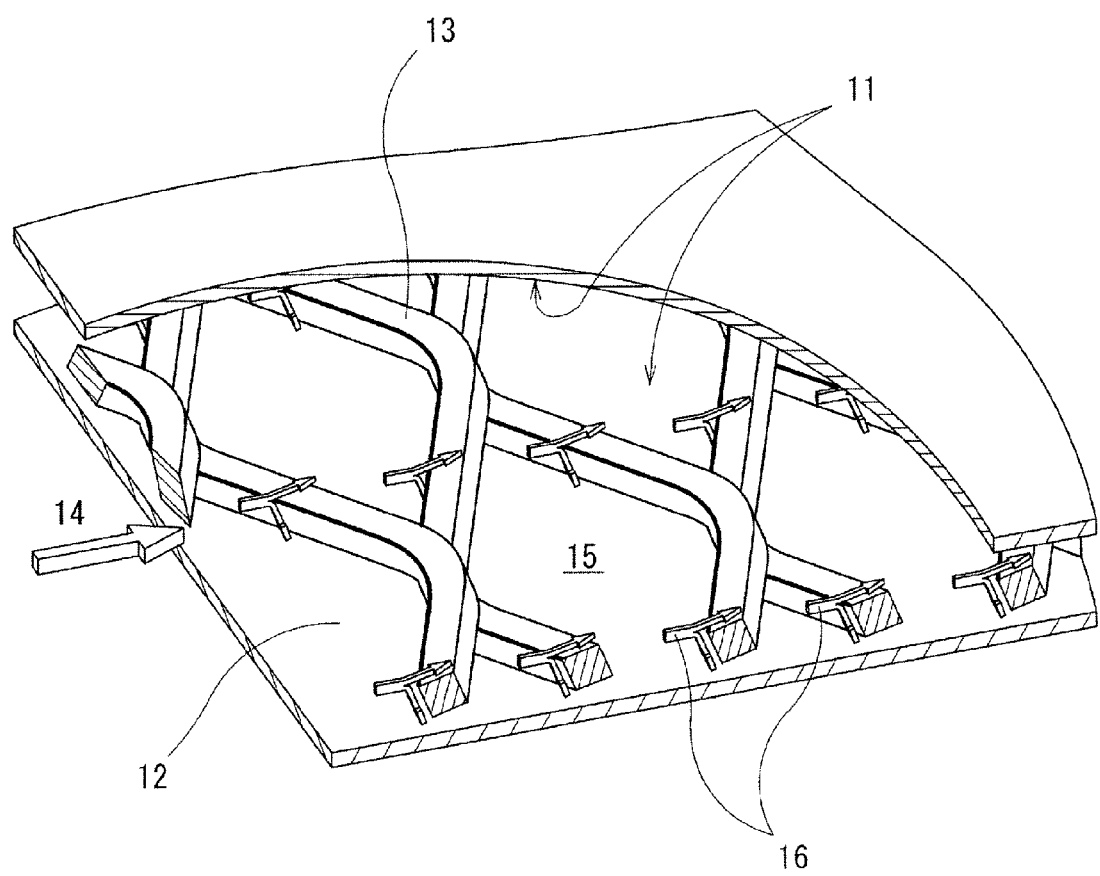
FIG. 1 is a partially cross-sectional perspective view showing a state wherein an expanded metal is arranged in a channel formed to lie between two planes for illustrating a method for improving fluid flow characteristics according to an embodiment of the present invention.
Figure 2:
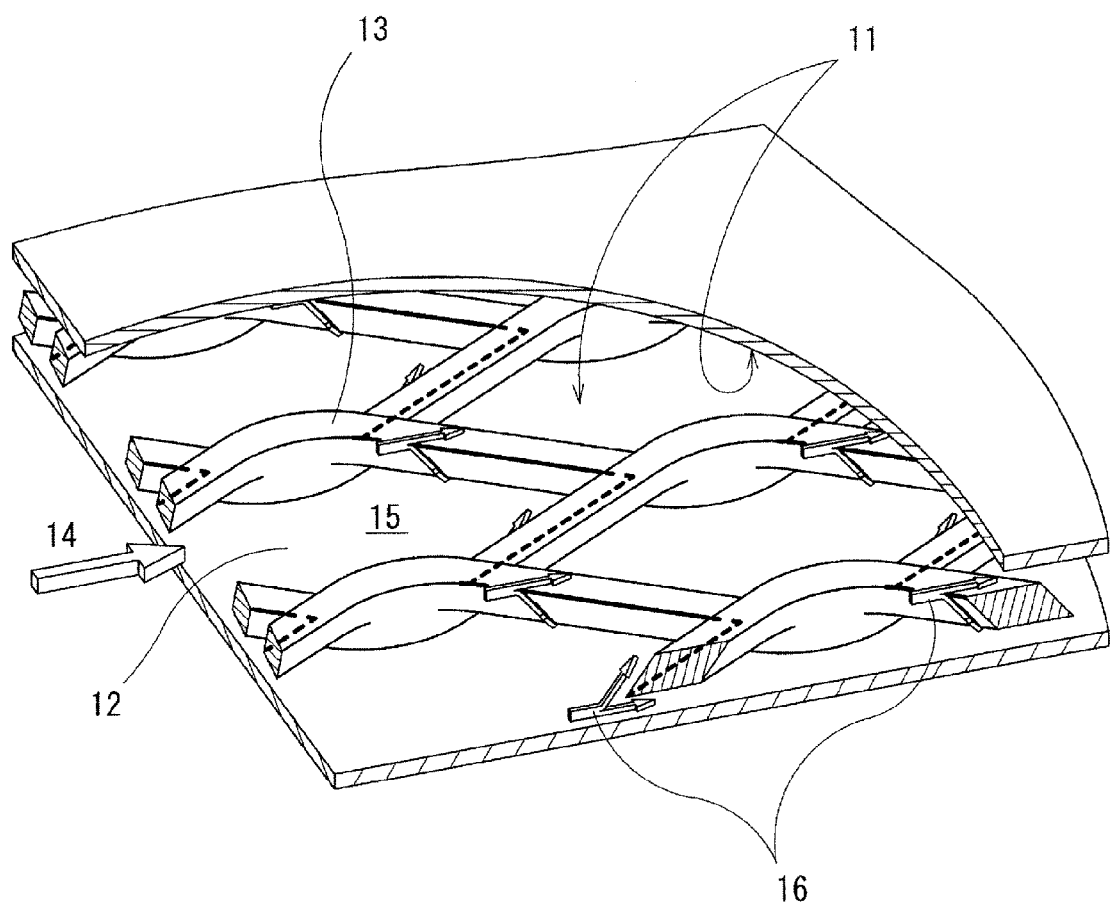
FIG. 2 is a partially cross-sectional perspective view showing a state wherein an expanded metal is arranged in a channel formed to lie between two planes for illustrating a method for improving fluid flow characteristics according to the embodiment.
Figure 3:
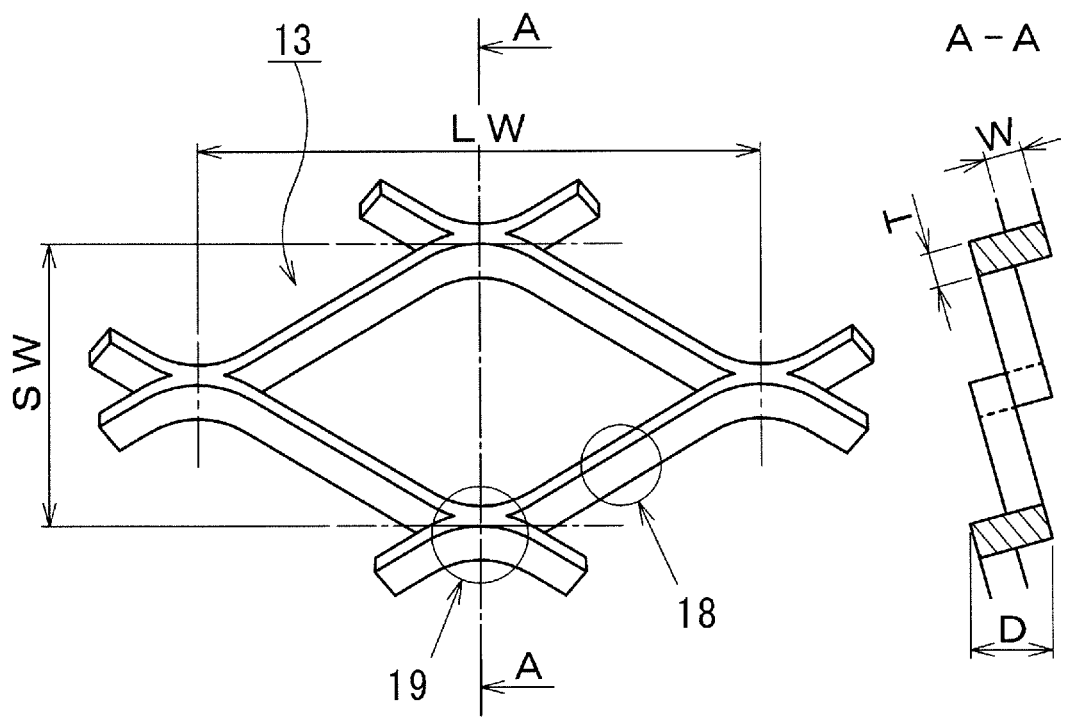
FIG. 3 comprises an elevation view and a cross-sectional view taken from line A-A showing an expanded metal according to the embodiment.

FIG. 1 is a partially cross-sectional perspective view showing Type II of a method for improving fluid flow characteristics according to an embodiment of the present invention, FIG. 2 is a partially cross-sectional perspective view showing Type I thereof, and FIG. 3 comprises an elevation view and a cross-sectional view taken from line A-A showing an expanded metal used in these methods.

Reference numeral 11 in the figures represents a channel plane. A channel 12 is formed to lie between these channel planes 11 and 11. In the channel 12, an expanded metal 13 is arranged.

Reference numeral 14 represents a fluid flow. In the channel 12, various boundary layers 15 are formed within the fluid, and with being affected by the expanded metal 13, local fluid flows 16 are formed.

Between Type I and Type II, how to arrange the expanded metal 13 in relation to the fluid flow 14 is different. In Type II shown in FIG. 1, the expanded metal 13 is arranged in the channel 12 in such a manner that the long way of an expanded metal mesh thereof crosses the fluid flow 14 at right angles.

In Type I shown in FIG. 2, the expanded metal 13 is arranged in the channel 12 in such a manner that the long way of the expanded metal mesh thereof is located parallel to the fluid flow 14.

The expanded metal 13 is manufactured by push-cutting slits in staggered arrangement on a steel plate using a blade and simultaneously stretching them so as to form meshes, resulting in a construction shown in FIG. 3.

The long way of a mesh is indicated as LW, the short way thereof as SW, the thickness as T, the width as W, and the whole thickness as D. The thin portion of the mesh is called a strand 18, while the thick portion of intersection of meshes is called a bond 19.

Figure 4:
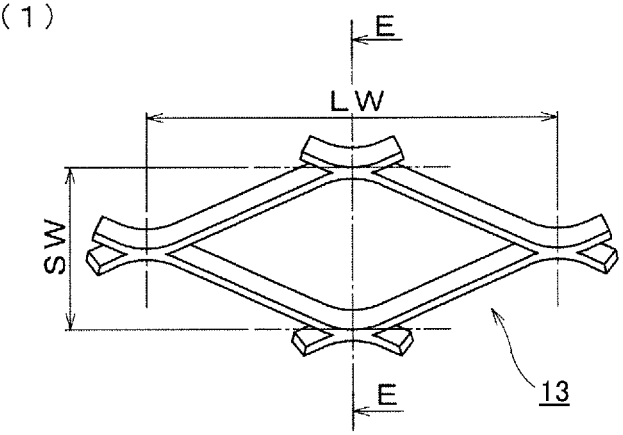
FIGS. 4(1)-4(3) are elevation views and side cross-sectional views showing three kinds of expanded metals according to the embodiment.
Figure 4:
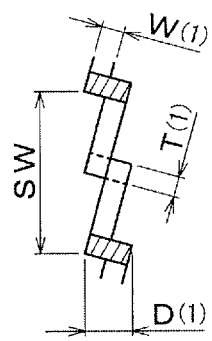
Figure 4:
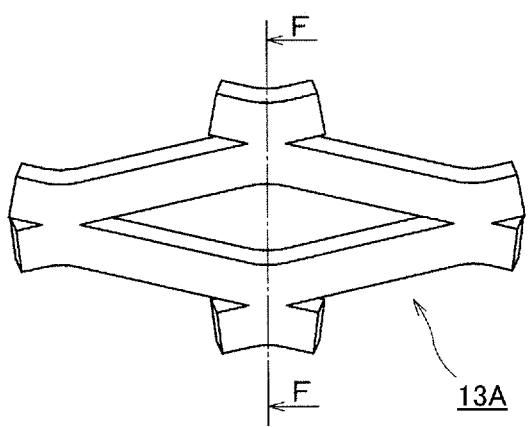
Figure 4:
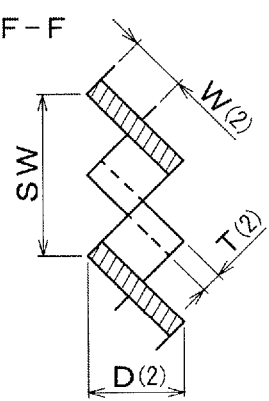
Figure 4:
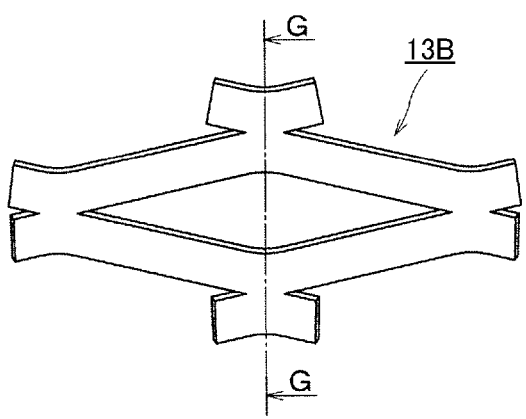
Figure 4:
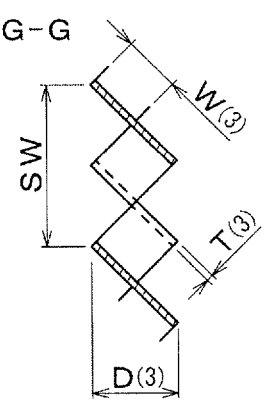
Figure 5:
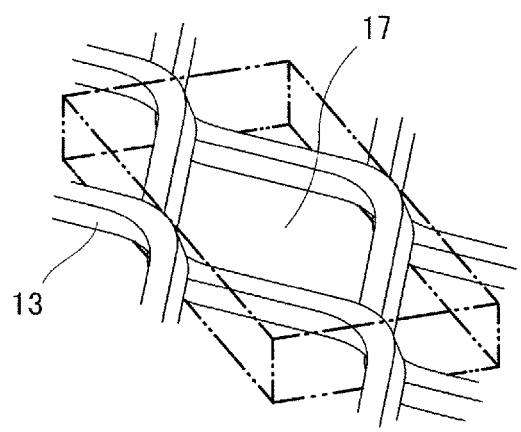
FIGS. 5(1)-5(3) are partially enlarged perspective views showing three kinds of expanded metals according to the embodiment.
Figure 5:
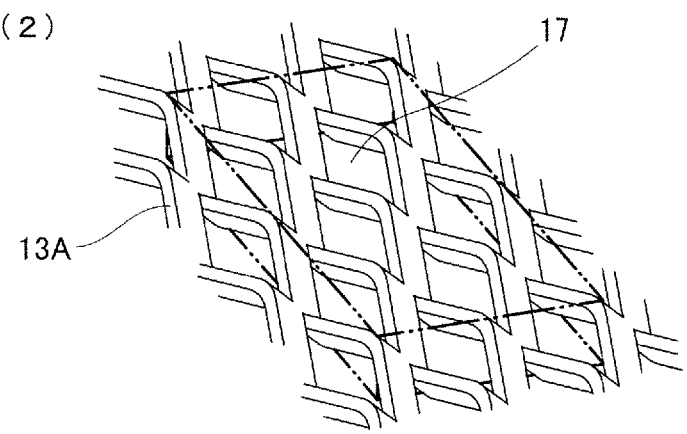
Figure 5:
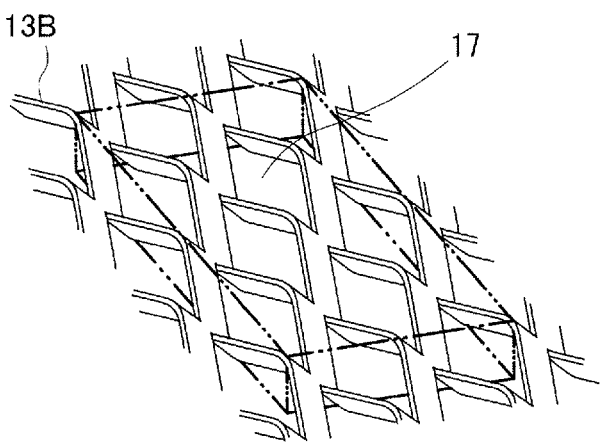

In the embodiment, by manufacturing and using varied expanded metals 13A and 13B, different from a standardized article, as shown in FIGS. 4(2) and 4(3), and FIGS. 5(2) and 5(3), the effect of the present invention can be enhanced.

The expanded metal 13A shown in FIG. 4(2) and FIG. 5(2) has a larger width W than the standardized article, while the expanded metal 13B shown in FIG. 4(3) and FIG. 5(3) has a smaller thickness T than the standardized article.

Figure 6:
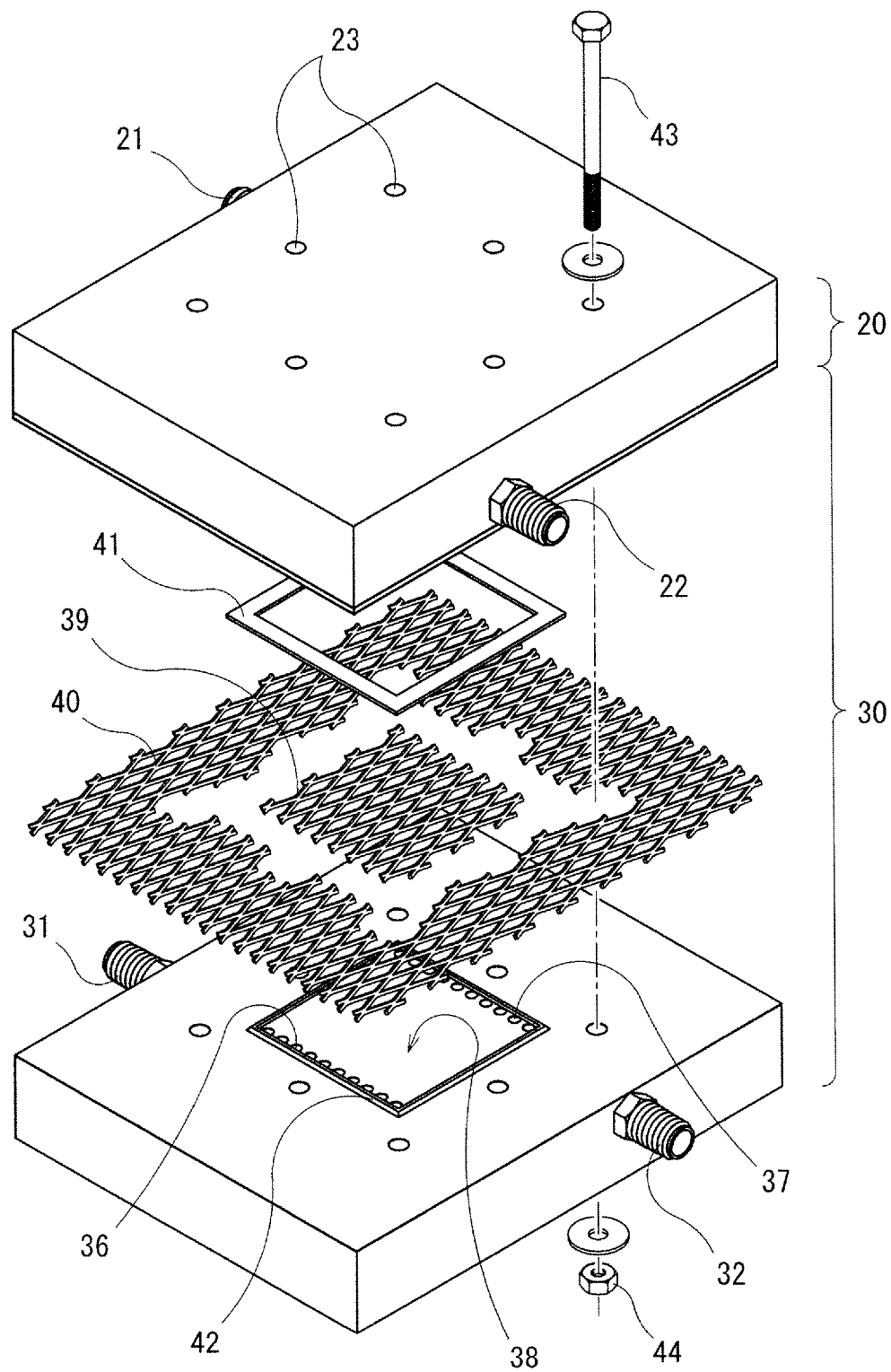
FIG. 6 is an exploded perspective view showing a heat flow measurement apparatus according to the embodiment.
Figure 7:
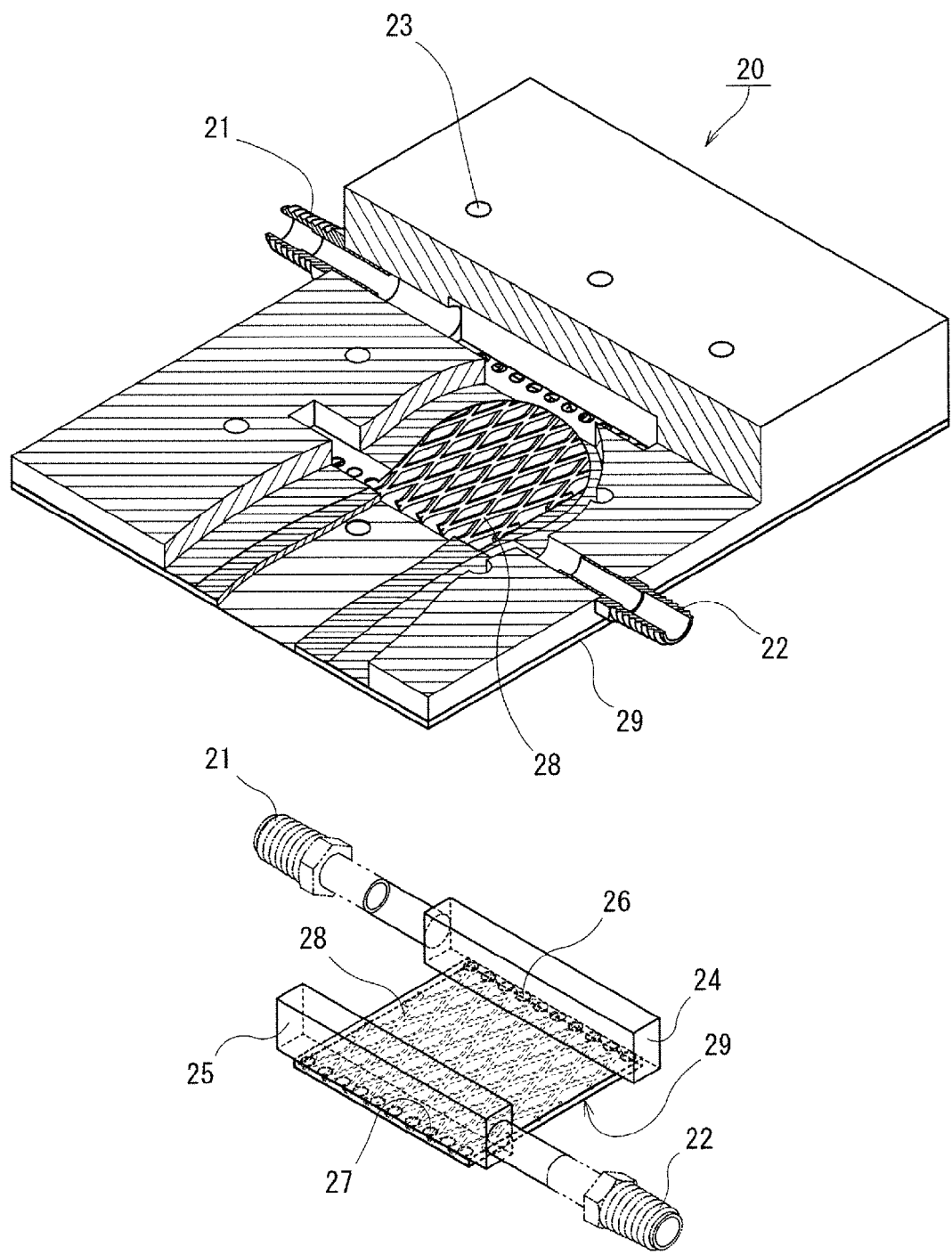
FIG. 7 is an exploded partially cross-sectional perspective view showing a fixed channel portion of the heat flow measurement apparatus according to the embodiment.
Figure 8:
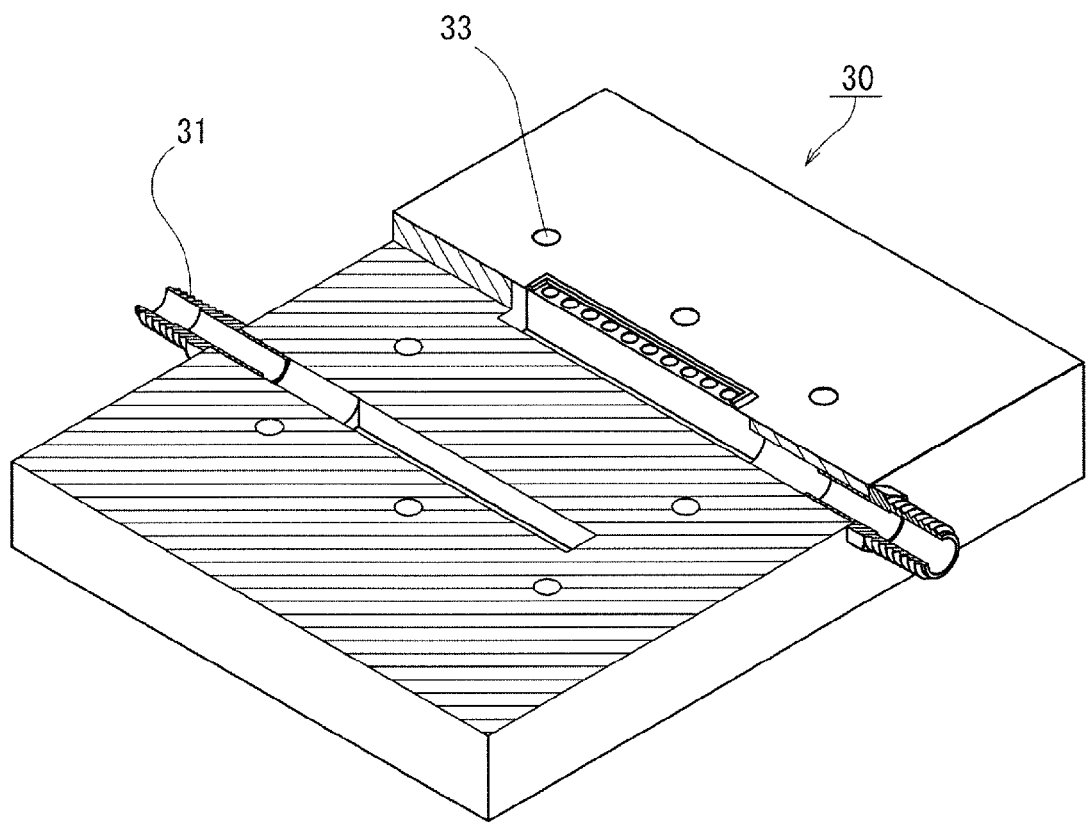
FIG. 8 is an exploded partially cross-sectional perspective view showing a variable channel portion of the heat flow measurement apparatus according to the embodiment.
Figure 8:
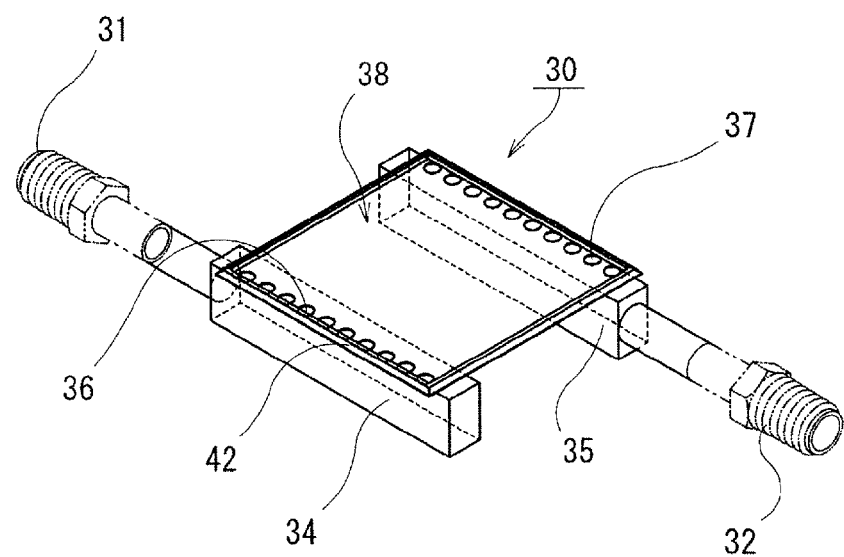
Figure 9:
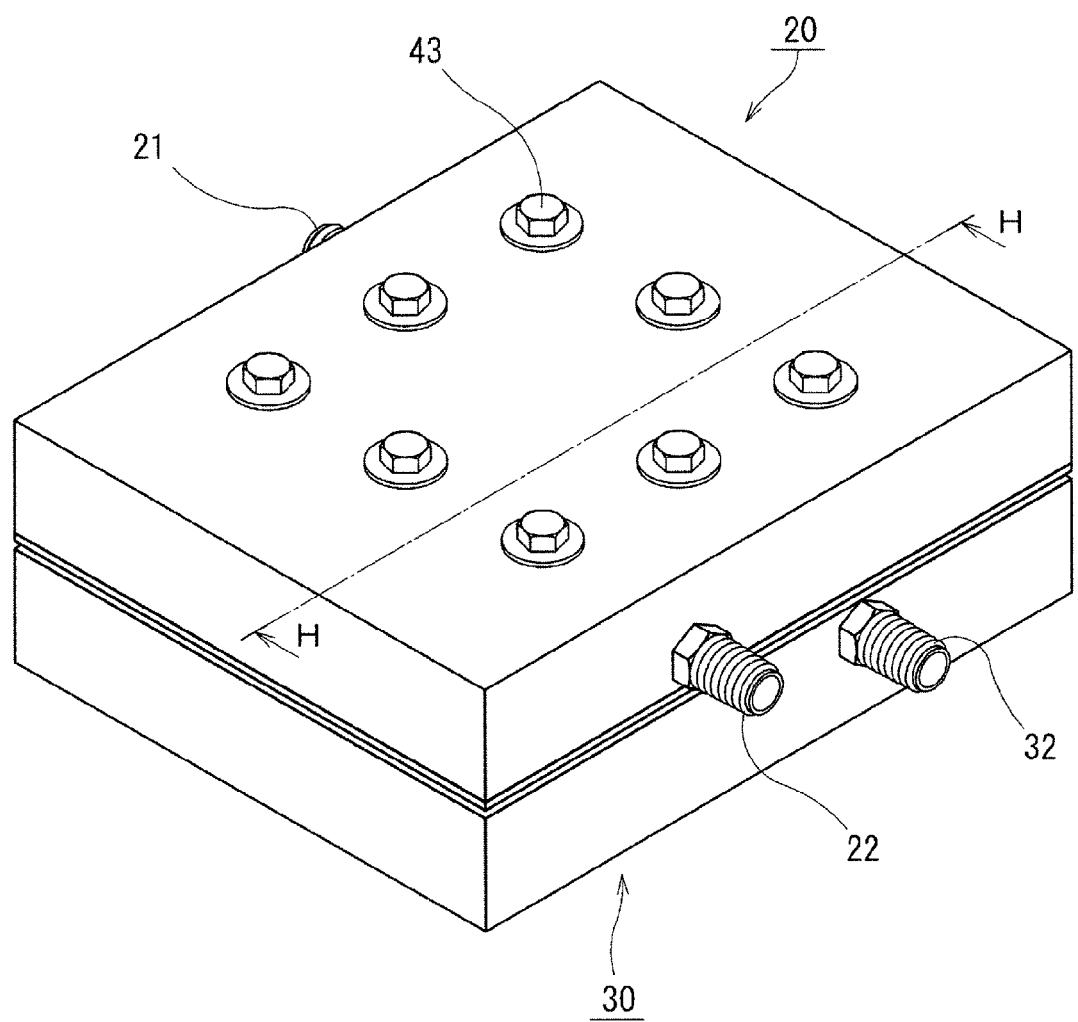
FIG. 9 is a perspective view showing the heat flow measurement apparatus according to the embodiment.
Figure 10:
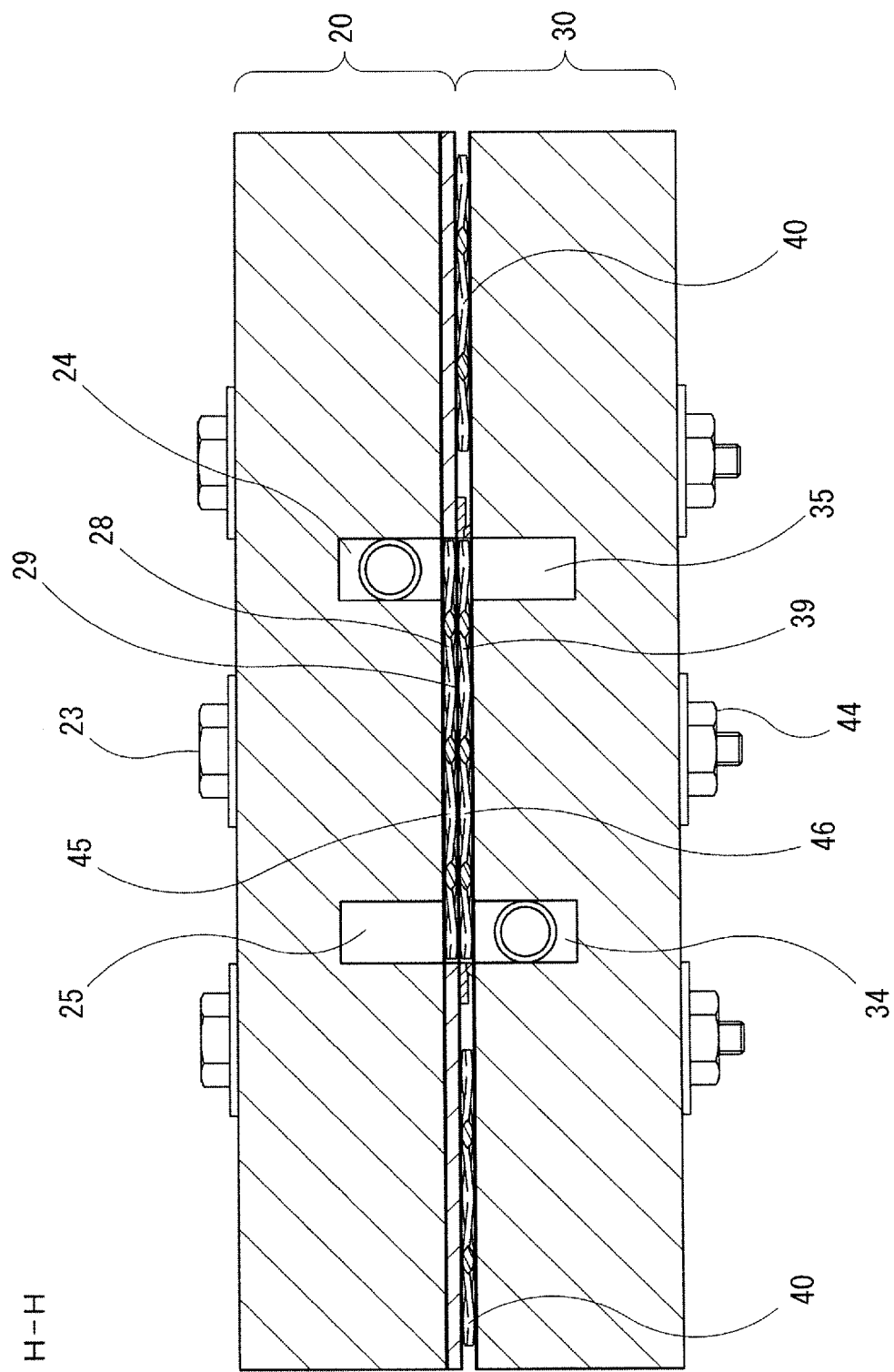
FIG. 10 is a cross-sectional view taken from line H-H showing the heat flow measurement apparatus according to the embodiment.

FIG. 6 is an exploded perspective view showing a heat flow measurement apparatus according to the embodiment, FIG. 7 is an exploded perspective view showing a fixed channel portion of the heat flow measurement apparatus, FIG. 8 is an exploded perspective view showing a variable channel portion of the heat flow measurement apparatus, FIG. 9 is an assembly perspective view showing the heat flow measurement apparatus, and FIG. 10 is a cross-sectional view taken from line H-H showing the heat flow measurement apparatus.

Reference numeral 20 represents a fixed channel portion, to which a fluid inlet line 21 and a fluid outlet line 22 are connected on the opposite sides thereof. And a plurality of bolt insertion holes 23 are formed vertically from the top thereof. A header 24 is connected to the fluid inlet line 21, while a header 25 is connected to the fluid outlet line 22. Fluid supply ports 26 are connected to the header 24, while fluid outflow ports 27 are connected to the header 25. Between the bottoms of the headers 24 and 25, a fixed expanded metal 28 and a heat-transfer plate 29 are disposed.

To a variable channel portion 30, a fluid inlet line 31 and a fluid outlet line 32 are connected on the opposite sides thereof. A plurality of bolt insertion holes 33 are formed vertically from the top thereof. These bolt insertion holes 33 are formed in places corresponding to the above plurality of bolt insertion holes 23. A header 34 is connected to the fluid inlet line 31, while a header 35 is connected to the fluid outlet line 32. Fluid supply ports 36 are formed in the header 34, while fluid outflow ports 37 are formed in the header 35. Between the tops of the headers 34 and 35, a rectangular channel plane 38 is formed. A fixed gasket 42 is disposed surrounding the rectangular channel plane 38, on which a variable expanded metal 39 is disposed. A variable gasket 41 is disposed around the variable expanded metal 39, and around the variable gasket 41, a variable spacer 40 is disposed.

Into the plurality of bolt insertion holes 23 and 33, respectively, bolts 43 are inserted and fixed with nuts 44. As shown in FIG. 10, a chilled water channel 45 is formed on the heat-transfer plate 29, while a hot water channel 46 is formed under the heat-transfer plate 29.

Figure 11:
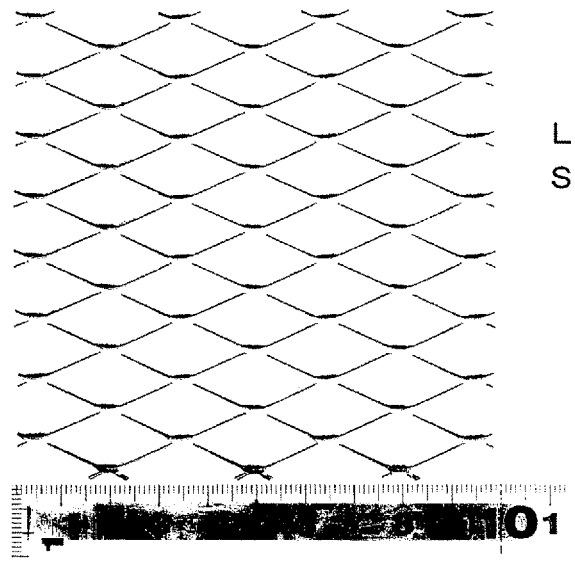
FIG. 11 is an elevation view showing an expanded metal (a) according to the embodiment.
Figure 12:
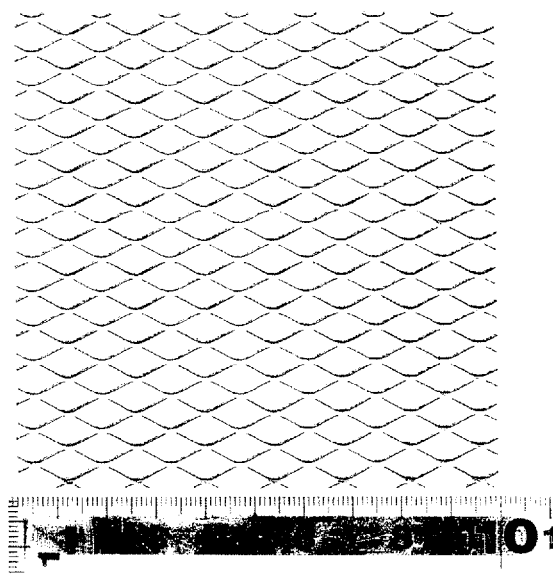
FIG. 12 is an elevation view showing an expanded metal (b) according to the embodiment.
Figure 13:
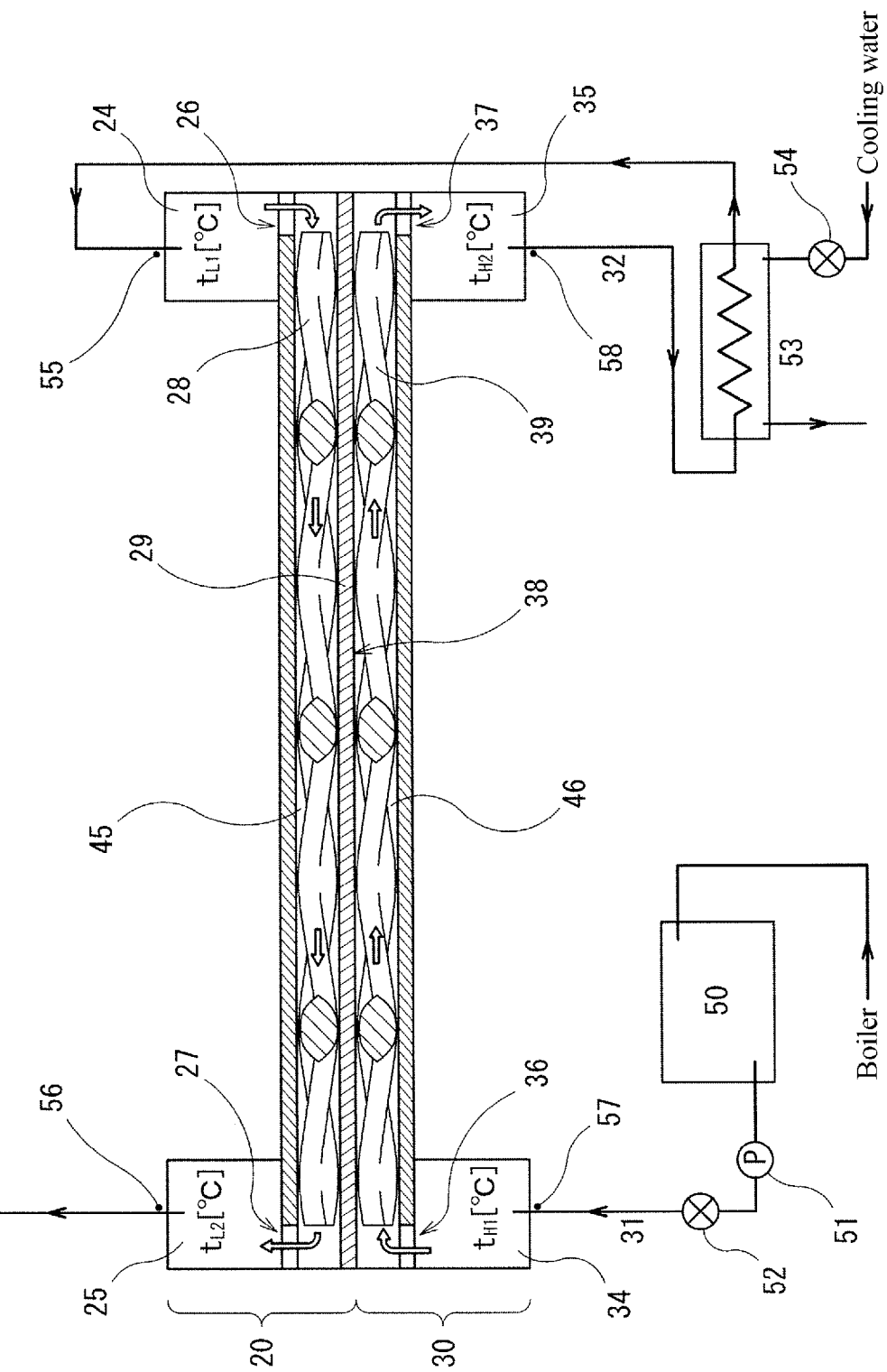
FIG. 13 is a cross-sectional view showing a heat flow measurement system according to the embodiment.

By adopting what are shown in FIGS. 11 and 12 as expanded metals and using a system shown in FIG. 13, the effect of the method for improving fluid flow characteristics according to the embodiment was confirmed.

In the system shown in FIG. 13, to the fluid inlet line 31 of the heat flow measurement apparatus shown in FIGS. 6-10, a hot water reservoir 50, a pump 51, a valve 52 and associated parts are further connected, while to the fluid outlet line 32 thereof, a cooling device 53 is connected. A valve 54 is interposed in a cooling water supply line to the cooling device 53.

On each of the headers 24, 25, 34 and 35, thermocouples 55, 56, 57 and 58 are disposed, respectively, so as to be able to detect hot water temperatures and cooling water temperatures in each place.

(1) Operation Procedures

Hot water (about 50° C.) supplied from a boiler is stored in the hot water reservoir 50. The water supply by the pump 51 is regulated by opening/closing of the valve 52 so as to be any given flow rate M[ml/sec].

The temperatures of running water within the headers 24, 25, 34 and 35 each are measured using the thermocouples 55, 56, 57 and 58 fitted into the inlets and outlets of the headers 24, 25, 34 and 35, respectively.

The flow rate of the cooling water entering into the cooling device 53 is regulated with the valve 54, so as to allow the difference between the running water temperature tH2[° C.] of the header 35 and the running water temperature tL1[° C.] of the header 24 to be 5[K]<(tL1−tH2)<7[K].

(2) The chilled water channel 45 side heat-transfer surface mean heat-transfer coefficient hLm[W/(m²·K)] for any given flow rate M[ml/sec] in the fixed channel portion 20 is determined.

In the fixed channel portion 20, the fixed expanded metal 28 shown in FIG. 11 is fixed in such a manner that the fluid flow direction is parallel to the long way of a mesh thereof ([Type I]) as shown in FIG. 2. The cross section of the channel is a rectangle having a long side length of 100 [mm] and a short side length of 3.3 [mm].

In the variable channel portion 30, the variable expanded metal 39 identical to that in the fixed channel portion 20 is arranged in the manner of [Type I]. Accordingly, the factors influencing the heat-transfer coefficient in the variable channel portion 30 and that in the fixed channel portion 20 are the same except for the running water temperatures. When the difference in running water temperature is 10° C. or less, for the hot water channel 46 side heat-transfer surface mean heat-transfer coefficient of hHm[W/(m²·K)], hLm≈hHm holds.

The heat-transfer plate 29 comprises an 18-Cr stainless steel plate, which is set to have a thickness d=0.0003 [m], a thermal conductivity λ=26 [W/(m·K)] and a heat-transfer area S=0.01 [m²].

The heat-transfer surface heat flux is expressed as q[W/m²], the logarithmic mean temperature difference between the hot and chilled water flows as ΔTm[K] and the overall heat-transfer coefficient as k[W/(m²·K)].

Concerning the above symbols, the following equation holds.

$$q = \frac{4.2M(t_{L2} - t_{L1})}{S} = \frac{4.2M(t_{H2} - t_{H1})}{S} [W/m^2] \quad \text{[Equation 1]}$$

$$\Delta Tm = \frac{(t_{H1} - t_{L2}) - (t_{H2} - t_{L1})}{\ln\{(t_{H1} - t_{L2})/(t_{H2} - t_{L1})\}}$$

$$\frac{1}{k} = \frac{1}{h_{Hm}} + \frac{d}{\lambda} + \frac{1}{h_{Lm}}$$

$$= \frac{d}{\lambda} + \frac{2}{h_{Lm}}$$

$$(\because h_{Hm} \approx h_{Lm})$$

$$q = k \cdot \Delta Tm$$

$$\therefore h_{Lm} = \frac{2}{\frac{\Delta Tm}{q} - \frac{d}{\lambda}} [W/(m^2 \cdot K)]$$

Figure 14:
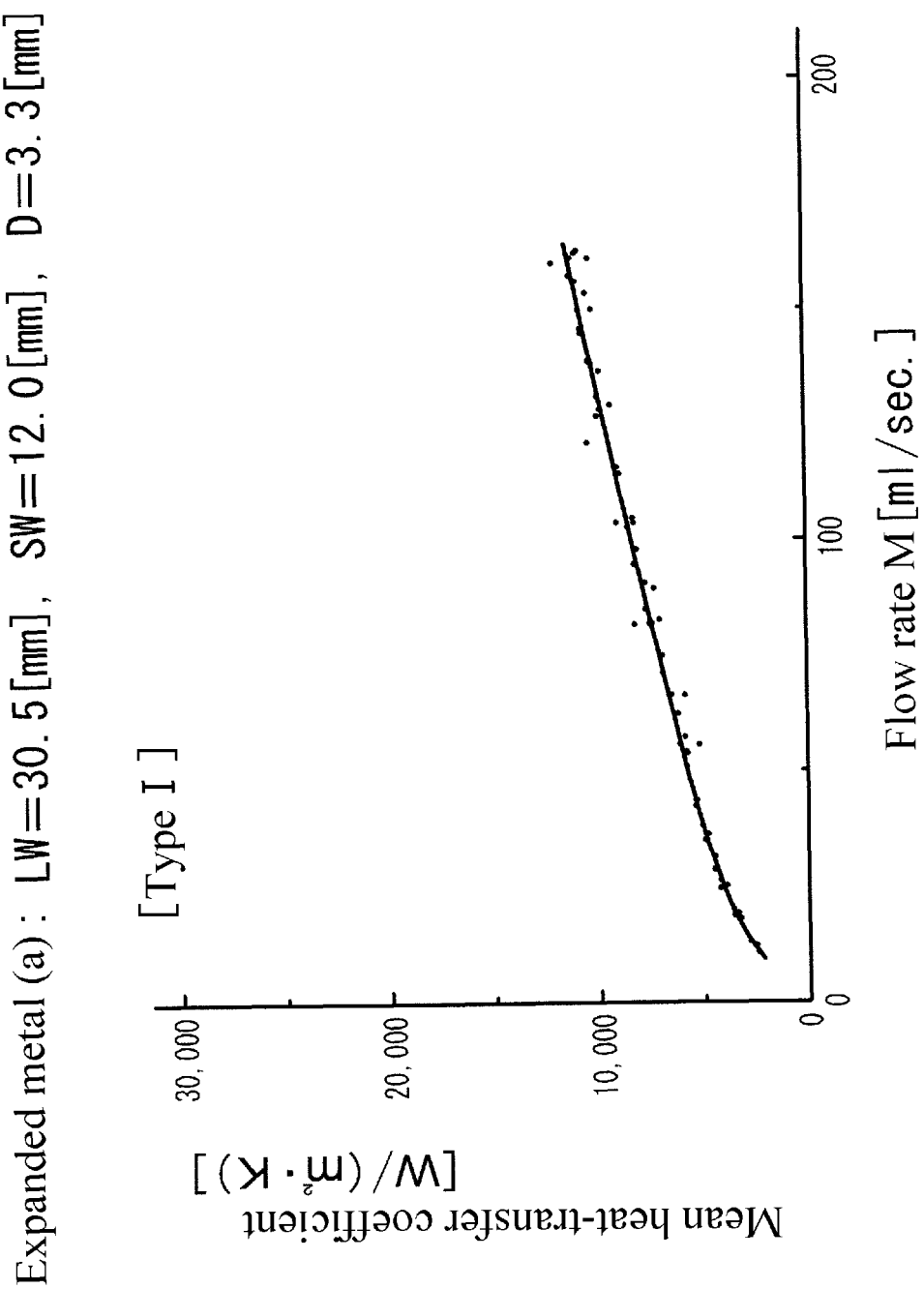
FIG. 14 is a graph showing the measurement result of heat flows according to the embodiment.

The chilled water channel 45 side heat-transfer surface mean heat-transfer coefficient hLm[W/(m²·K)] for any given flow rate M[ml/sec] in the fixed channel portion 20 obtained using the measured values and the equation is shown in FIG. 14.

(3) Concerning two kinds of expanded metals (a) and (b) shown in FIGS. 11 and 12, respectively, the hot water channel 46 side heat-transfer surface mean heat-transfer coefficient hHm[W/(m²·K)] for any given flow rate M[ml/sec] in the variable channel portion 30 is determined by channel type.

[Type I]: The fluid flow is parallel to the long way of a mesh, shown in FIG. 2.

[Type II]: The fluid flow crosses the long way thereof at right angles, shown in FIG. 1.

[Type III]: Corresponding to a comparative example to [Type I] and [Type II]. A channel of rectangular cross section comprising a hollow rectangular parallelpiped. Its hollow is secured with a variable spacer having the same thickness as the expanded metals (a) and (b), respectively.

The heat-transfer surface mean heat-transfer coefficient hLm[W/(m²·K)] for any given flow rate M[ml/sec] in the fixed channel portion 20 is obtained from a solid line of a graph shown in FIG. 14, and the hot water channel 46 side heat-transfer surface mean heat-transfer coefficient hHm[W/(m²·K)] for any given flow rate M[ml/sec] in the variable channel portion 30 is obtained by channel type using the following equation.

$$q = \frac{4.2M(t_{L2} - t_{L1})}{S} = \frac{4.2M(t_{H2} - t_{H1})}{S} [W/m^2] \quad \text{[Equation 2]}$$

$$\Delta Tm = \frac{(t_{H1} - t_{L2}) - (t_{H2} - t_{L1})}{\ln\{(t_{H1} - t_{L2})/(t_{H2} - t_{L1})\}}$$

$$\frac{1}{k} = \frac{1}{h_{Hm}} + \frac{d}{\lambda} + \frac{1}{h_{Lm}}$$

$$q = k \cdot \Delta Tm$$

$$\therefore h_{Hm} = \frac{1}{\frac{\Delta Tm}{q} - \frac{d}{\lambda} - \frac{1}{h_{Lm}}} [W/(m^2 \cdot K)]$$

Figure 15:
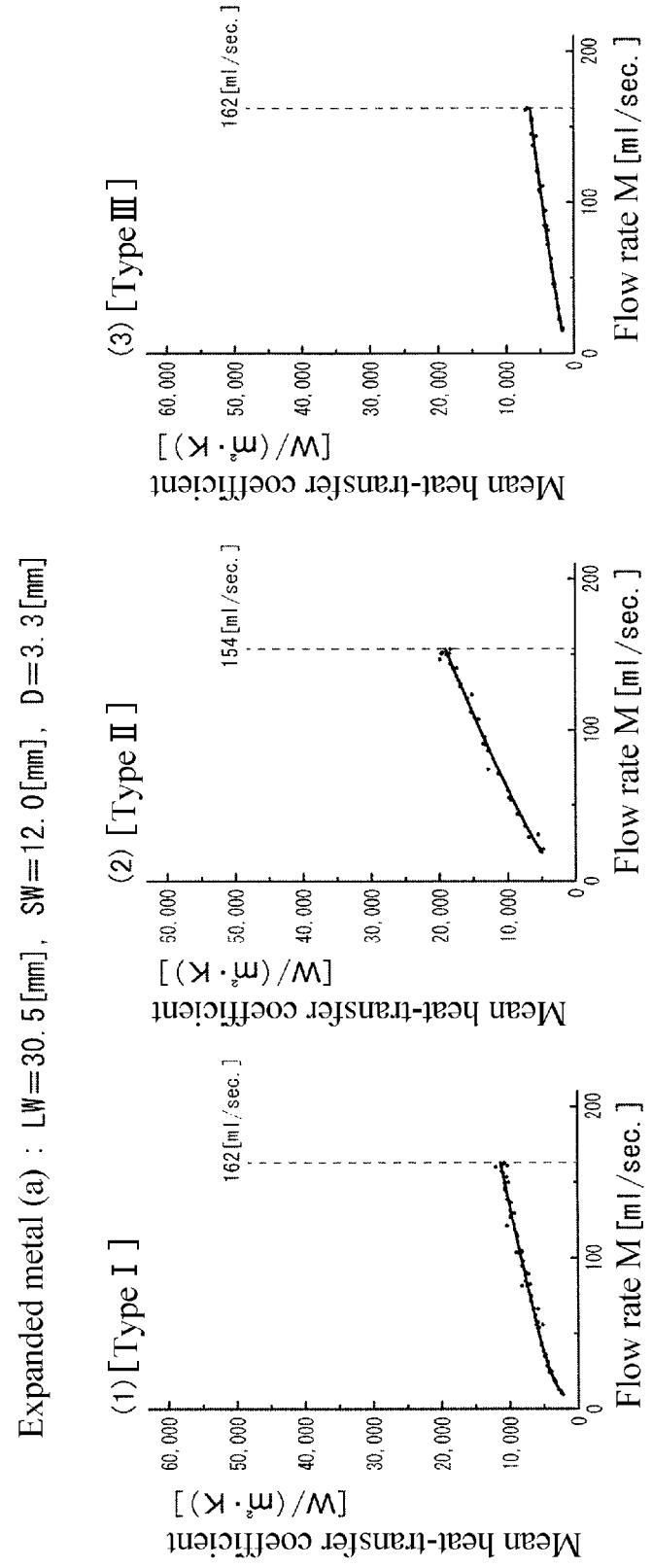
FIGS. 15(1)-15(3) are graphs showing the measurement results of heat flows according to the embodiment and a comparative example.

The hot water channel 46 side heat-transfer surface mean heat-transfer coefficients hHm[W/(m²·K)] by channel type as to the expanded metal (a) are shown in FIG. 15. The broken line drawn in parallel to the y axis in the graph indicates the maximum flow rate when the valve 52 is fully opened.

Figure 16:
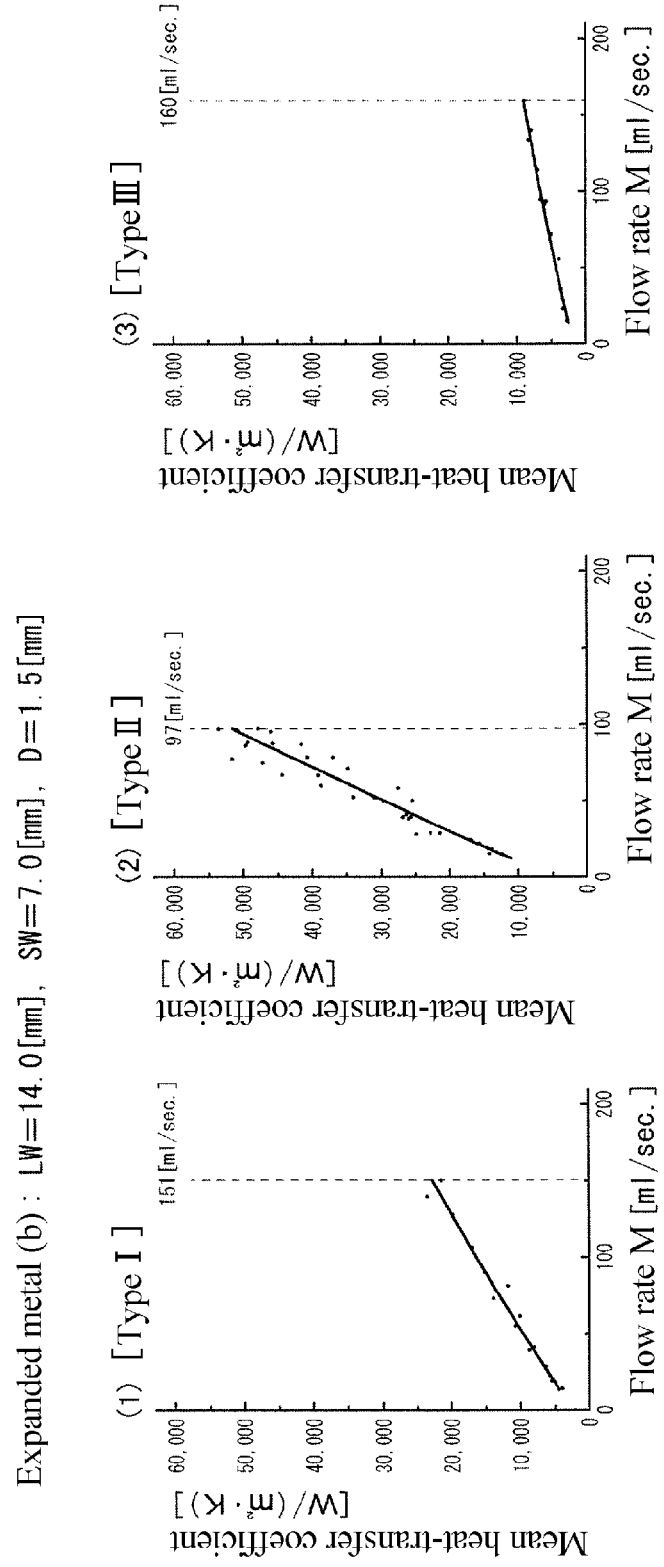
FIGS. 16(1)-16(3) are graphs showing the measurement results of heat flows according to the embodiment and the comparative example.

The hot water channel 46 side heat-transfer surface mean heat-transfer coefficients hHm[W/(m²·K)] by channel type as to the expanded metal (b) are shown in FIG. 16. The broken line drawn in parallel to the y axis in the graph indicates the maximum flow rate when the valve 52 is fully opened.

Figure 15A:
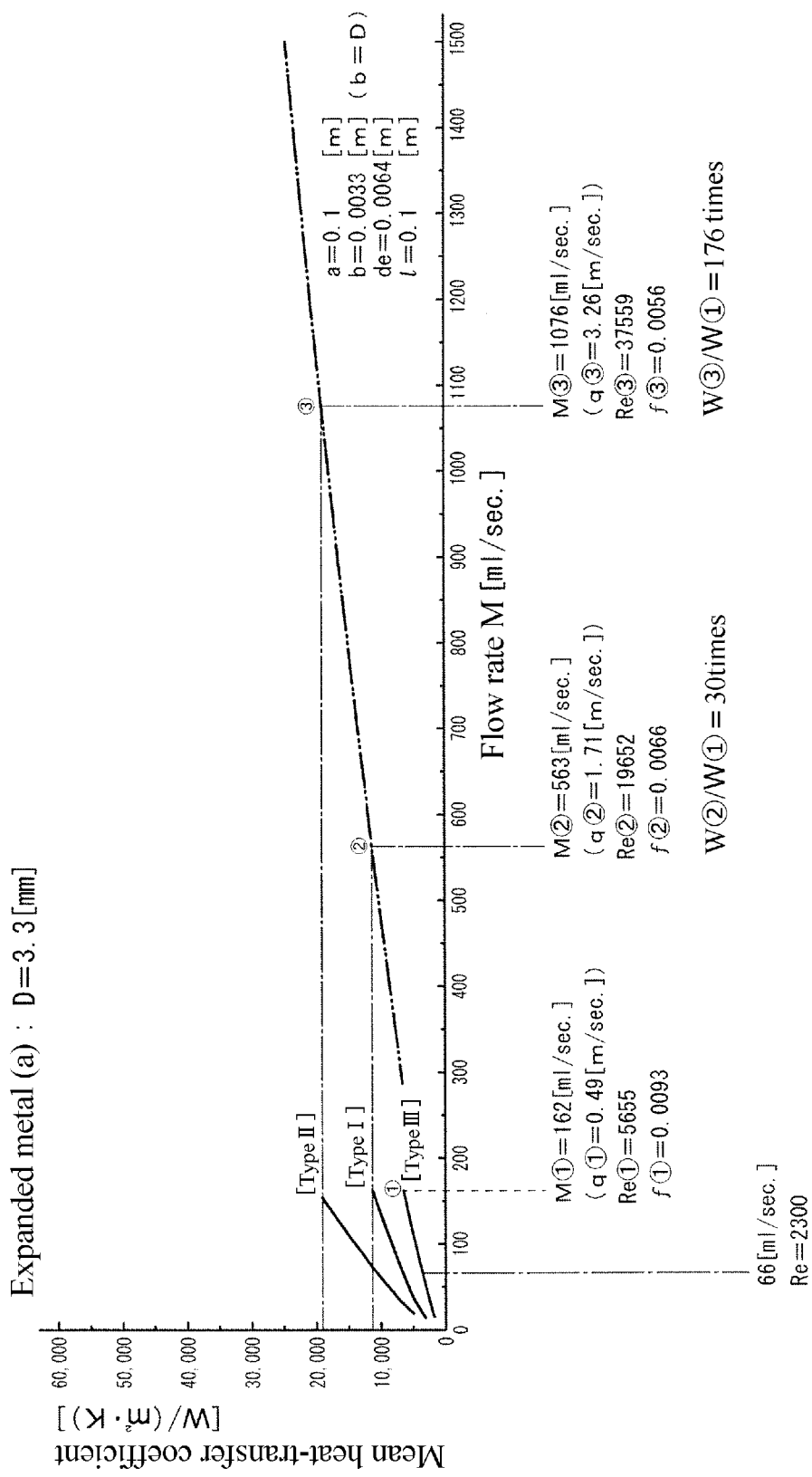
FIG. 15*a* is a graph showing the measurement results of heat flows according to the embodiment and the comparative example.
Figure 16A:
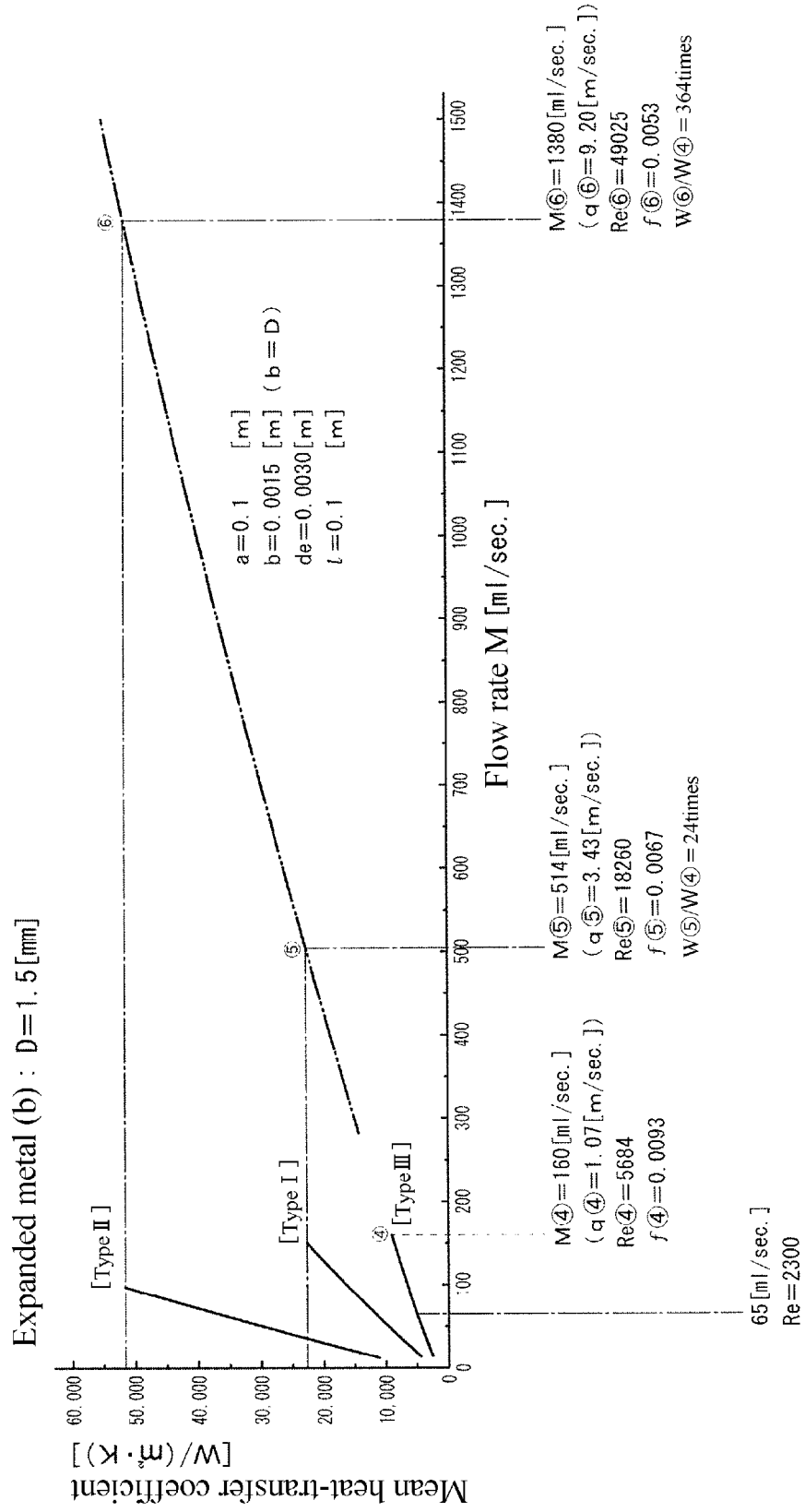
FIG. 16*a* is a graph showing the measurement results of heat flows according to the embodiment and the comparative example.

The thick two-dot chain lines in FIGS. 15a and 16a indicate the heat-transfer coefficients of the fluid flow of [Type III] in the channel of rectangular cross section with a long side length of a[m] and a short side length of b[m] shown in each figure for any given flow rate M[ml/sec] obtained from calculation. The heat-transfer coefficient is obtained by acquiring the Nusselt number Nu from the Petukhov equation shown in the following [Equation 3] and using a relation shown in the following [Equation 4].

Petukhov equation (Petukhov, B.S., [Equation 3]
Advances in Heat Transfer, 6(1970), 523)

$$Nu = \frac{(f/2)\mathrm{Re} \cdot Pr}{1.07 + 12.7\sqrt{f/2}\,(Pr^{2/3} - 1)}$$

$(10^4 < \mathrm{Re} < 10^6,\ 0.5 < Pr < 2000)$

Nu: Nusselt number
Re: Reynolds number
Pr: Prandtl number
f: Pipe friction coefficient $f = (3.64\log_{10}\mathrm{Re} - 3.28)^{-2}$ $$Nu = h \cdot de / \lambda \qquad [\text{Equation 4}]$$

h: Heat-transfer coefficient [W/m² · K]
de: Equivalent diameter [m]
λ: Thermal conductivity of fluid [W/m · K]

$de = 4a \cdot b / 2(a + b)$ a: Long side length of the rectangular channel cross section [m]
b: Short side length of the rectangular channel cross section [m]

The fluid running within a horizontal tube generates an energy loss because of friction with the tube wall. When a pressure loss incident to that is expressed as Δ p[Pa], Δp[Pa] can be expressed using Darcy-Weisbach equation as the following [Equation 5].

$$\Delta p = f \frac{l}{de} \cdot \frac{1}{2}\rho u^2 \qquad [\text{Equation 5}]$$

f: Pipe friction coefficient $f = (3.64\log_{10}\mathrm{Re} - 3.28)^{-2}$ de: Equivalent diameter [m]

l: Passage [m]

u: Flow velocity [m/sec]

ρ: Fluid density [kg/m³]

The power W[W] of the pump sending the fluid at a flow rate M[ml/sec] against this pressure loss is obtained from W=M×10⁻⁶·Δp[W].

As shown in FIG. 15a, compared to W① at the point ①, the pump power of W②/W①=30 times is required at the point ②. At the point ③, the pump power of W③/W①=176 times is required.

In this example, with the pump power at the point ①, the heat-transfer coefficient of ② or ③ can be obtained. The extremely high effectiveness (176 times efficiency) of the present invention through a local turbulent flow acceleration effect is shown.

Similarly, in FIG. 16a, compared to W④ at the point ④, the pump power of W⑤/W④=24 times is required at the point ⑤. At the point⑥, the pump power of W⑥/W④=364 times is required.

In this example, with the pump power at the point ④, the heat-transfer coefficient of ⑤ or ⑥ can be obtained. The extremely high effectiveness (364 times efficiency) of the present invention through a local turbulent flow acceleration effect is shown.

The heat-transfer coefficient becomes larger as the thickness of the temperature boundary layer becomes smaller, leading to a smaller thermal resistance in the temperature boundary layer portion.

As the flow rate increases and the Reynolds number Re becomes larger, like ② and ③ in FIG. 15a, and ⑤ and ⑥ in FIG. 16a, the turbulent flow is accelerated and the thickness of the temperature boundary layer decreases, leading to a larger heat-transfer coefficient.

In these examples, it can be said that the expanded metals (a) and (b) cause extremely large local turbulent flow acceleration effects.

In the case of [Type I] shown in FIG. 2, the local fluid flows 16 split by the upstream side strand edges (indicated with thick solid lines) heading toward the channel planes 11 are formed uniformly to both the channel planes 11 and 11, and since the wedge angle of the upstream side strand edge (indicated with a thick solid line) portion of the strand cross section parallel to the flow is small, the impact angle of the local fluid flow 16 to the channel plane 11 is small. As a result, the circulation resistance is small, but the turbulent flow acceleration effect which makes the temperature boundary layer 15 thinner is poorer than that of [Type II] shown in FIG. 1.

In the case of [Type II] shown in FIG. 1, the local fluid flows 16 split by the upstream side strand edges (indicated with thick solid lines) heading toward the channel planes 11 are limited to flows toward one plane. And since the wedge angle of the upstream side strand edge (indicated with a thick solid line) portion of the strand cross section parallel to the flow is large, the circulation resistance becomes large. However, the turbulent flow acceleration effect which makes the temperature boundary layer 15 thinner is extremely large and excellent.

When comparing and considering FIGS. 15 and 16, it is presumed that the smaller the mesh size of the expanded metal is, the larger the turbulent flow acceleration effect becomes. When choosing a standardized expanded metal commercially available having a small mesh size, the whole thickness D becomes relatively small.

FIG. 4(1) shows a general standardized expanded metal 13. Even if the expanded metals have the same mesh size, with an increased width W nonstandard like those in FIGS. 4(2) and 4(3), the whole thickness D thereof can be increased. In the case of the same mesh size, when the length of the hypotenuse of an isosceles right triangle having the other two sides of the width W is set to be half of the short way SW of a mesh, the whole thickness D thereof becomes a maximum value.

FIG. 5(1) is a perspective view of the expanded metal 13 shown in FIG. 4(1). Like the expanded metals shown in FIGS. 5(2) and 5(3), by increasing the width W, the mesh size can be made smaller while the whole thickness D is kept the same.

Compared with the expanded metal in FIG. 5(1), using that in FIG. 5(2) or 5(3), the density of the local fluid flows 16 heading toward the channel planes 11 increases, resulting in enhancing the local turbulent flow acceleration effect of the expanded metal.

The local turbulent flow acceleration effects of the expanded metals 29 and 38 shown in the examples, effectively work not only in a single-phase flow wherein a gas or a liquid flows in a single phase, but also in a gas-liquid two-phase flow. In the gas-liquid two-phase flow, a temperature boundary layer or a density boundary layer in a liquid film flowing along a plane is stirred by turbulent gas, and the heat transfer/mass transfer within the liquid film is accelerated.

Figure 17:
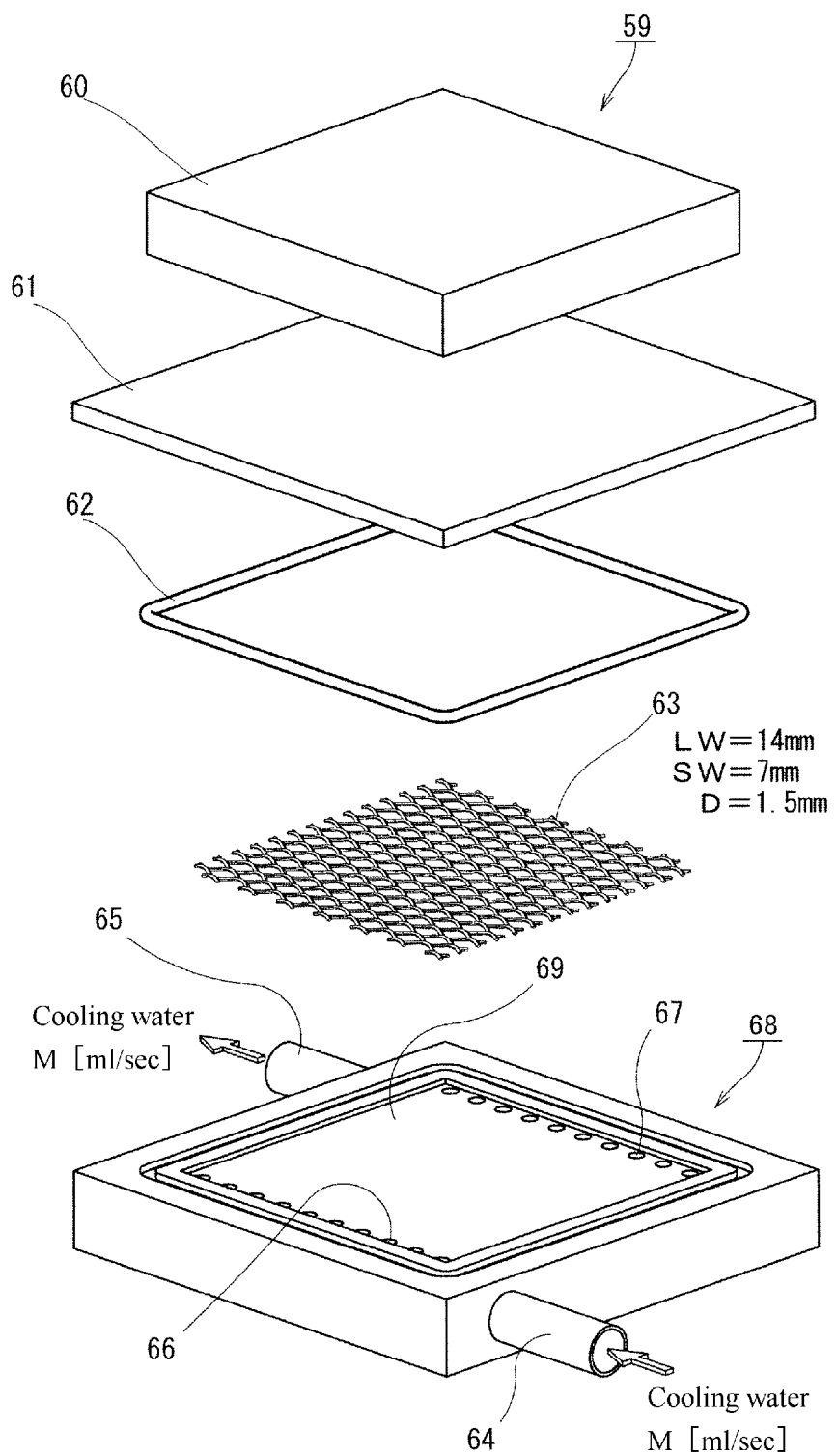
FIG. 17 is an exploded perspective view showing a cooling device (heat exchanger) according to the embodiment.

FIG. 17 shows an example of a cooling apparatus which cools a heat-generating body such as a semiconductor power module to which the method for improving fluid flow characteristics according to the present invention is applied. A radiation plate 61 is disposed in contact with a heat-generating body 60. Beneath the radiation plate 61, an expanded metal 63 surrounded by an O ring 62 is disposed. And to the expanded metal 63, a cooling unit 68 in the shape of a thin box is connected. To the sides of the cooling unit 68, a cooling water inlet line 64 and a cooling water outlet line 65 are connected, while on the top of the cooling unit 68, fluid supply ports 66 and fluid outflow ports 67 are formed.

A cooling channel 69 in which cooling water flows has a rectangular cross section with a long side length of 100 [mm] and a short side length of 1.5 [mm], and its passage is 100 [mm] In the cooling channel 69, an expanded metal (b) shown in FIG. 12 is arranged in the manner of [Type II] shown in FIG. 1.

The cooling channel 69 side radiation surface of the radiation plate 61 is directly cooled by the cooling water, while to the other surface of the radiation plate 61, the heat-generating body 60 is fitted by brazing or soldering.

When the cooling water flow rate M=100 [ml/sec], the heat-transfer coefficient of the cooling water is about 50000 [W/(m$^2$·K)] obtained from the graph of [Type II] in FIG. 16. That is, a high-performance cooling apparatus 59 having a thermal resistance between the radiation surface of the radiation plate 61 and the cooling water of 0.002 [K/W] can be realized. That apparatus makes it possible to conduct cooling of 5 [kW] per 100 [cm$^2$] of cooling area, when there is a temperature difference of 10 [K] between the radiation surface temperature of the radiation plate 61 and the cooling water.

When the cooling water flow rate M=200 [ml/sec], the cooling apparatus 59 can be made higher-performance. That apparatus makes it possible to conduct cooling of about 10 [kW] per 100 [cm$^2$] of cooling area, when there is a temperature difference of 10 [K] between the radiation surface temperature of the radiation plate 61 and the cooling water.

For information, in order to produce a cooling apparatus having the same performance without arranging an expanded metal 63 in a cooling channel 69, the short side length of a rectangular channel should be mathematically 0.2 [mm], leading to significant problems of pressure loss and blinding.

Figure 18:
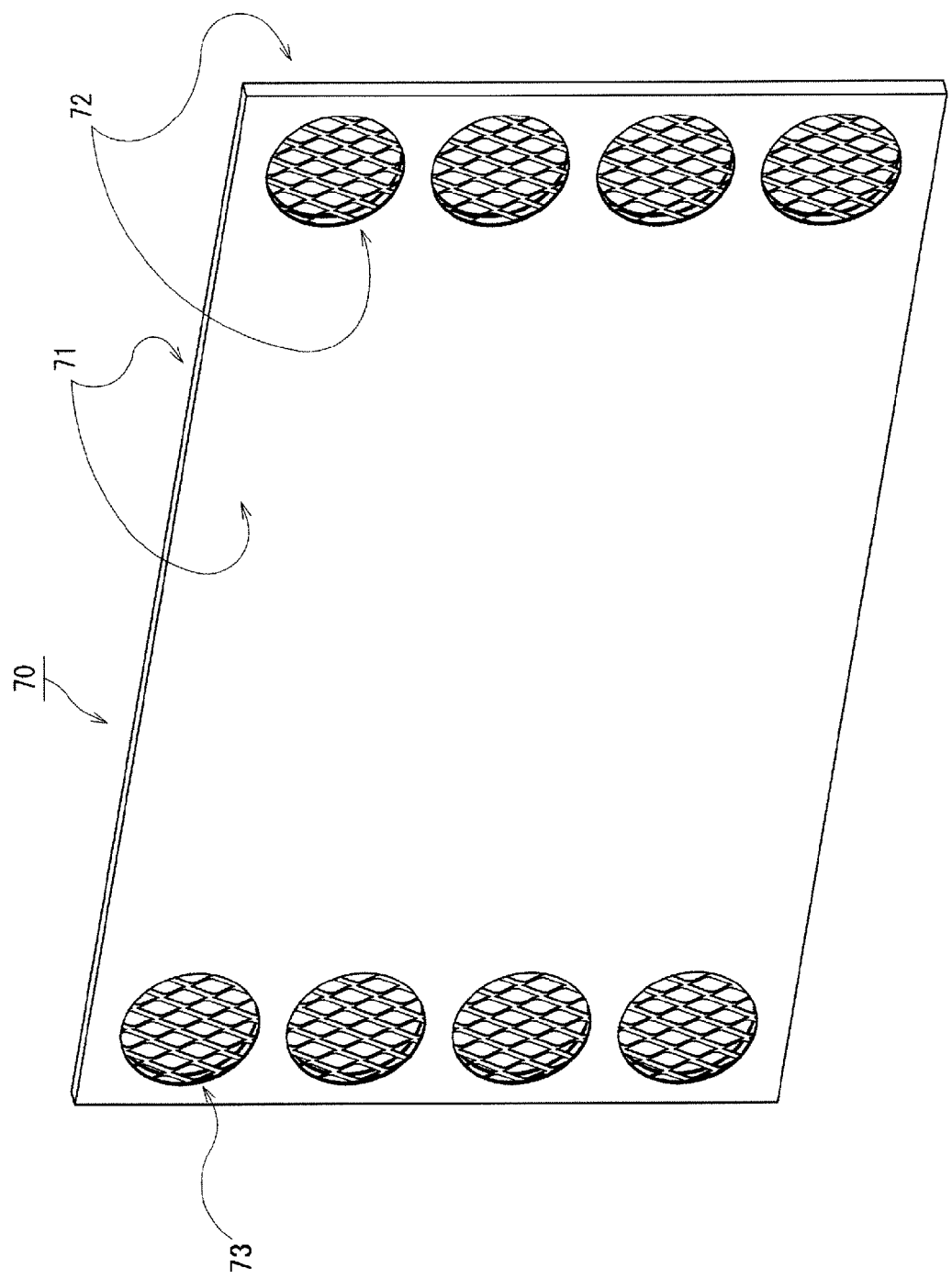
FIG. 18 is a perspective view showing a plate type heat exchanger tube according to the embodiment.

FIG. 18 shows a plate type heat exchanger tube according to the embodiment. The plate type heat exchanger tube 70 has heat-transfer surfaces 71 and 71, and in the vicinities of one side end portions of the heat-transfer surfaces 71 and 71, a plurality of fluid inflow ports 72 are formed, while a plurality of fluid outflow ports 73 are formed in the vicinities of the other side end portions thereof.

Figure 18A:
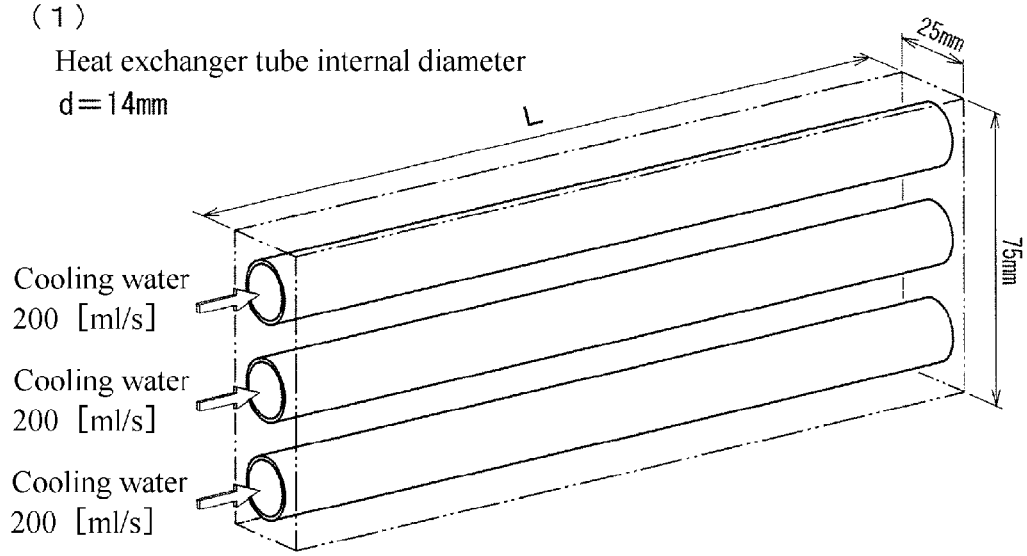
FIGS. 18*a*(1)-18*a*(3) are perspective views showing a tube type heat exchanger tube, and part of plate type heat exchanger tubes according to the comparative example and the embodiment, respectively.
Figure 18A:
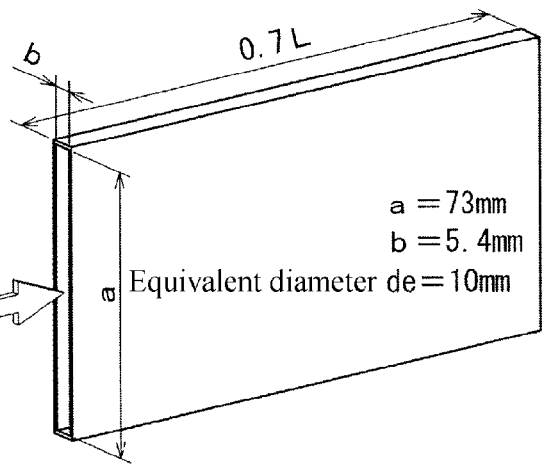
Figure 18A:
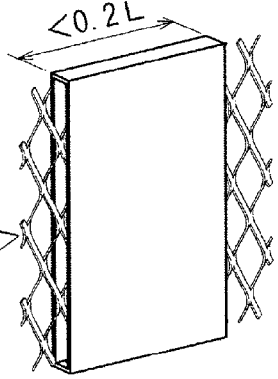

In FIGS. 18*a*(1)-18*a*(3), concerning a heat exchanger tube group comprising round tubes as heat exchanger tubes (FIG. 18*a*(1)), a plate type heat exchanger tube (FIG. 18*a*(2)) and a plate type heat exchanger tube according to the embodiment of the present invention (FIG. 18*a*(3)), the heat exchanger tube sizes thereof to realize the same thermal resistance therein are compared with one another. It is found that the heat-transfer performance within the plate type heat exchanger tube according to the embodiment (FIG. 18*a*(3)) is greatly improved, about 25 times higher than the heat exchanger tube group (FIG. 18*a*(1)). However, without the heat-transfer performance outside the plate type heat exchanger tube 70 simultaneously improved, the property of the plate type heat exchanger tube 70 according to the embodiment cannot be sufficiently shown.

Figure 19:
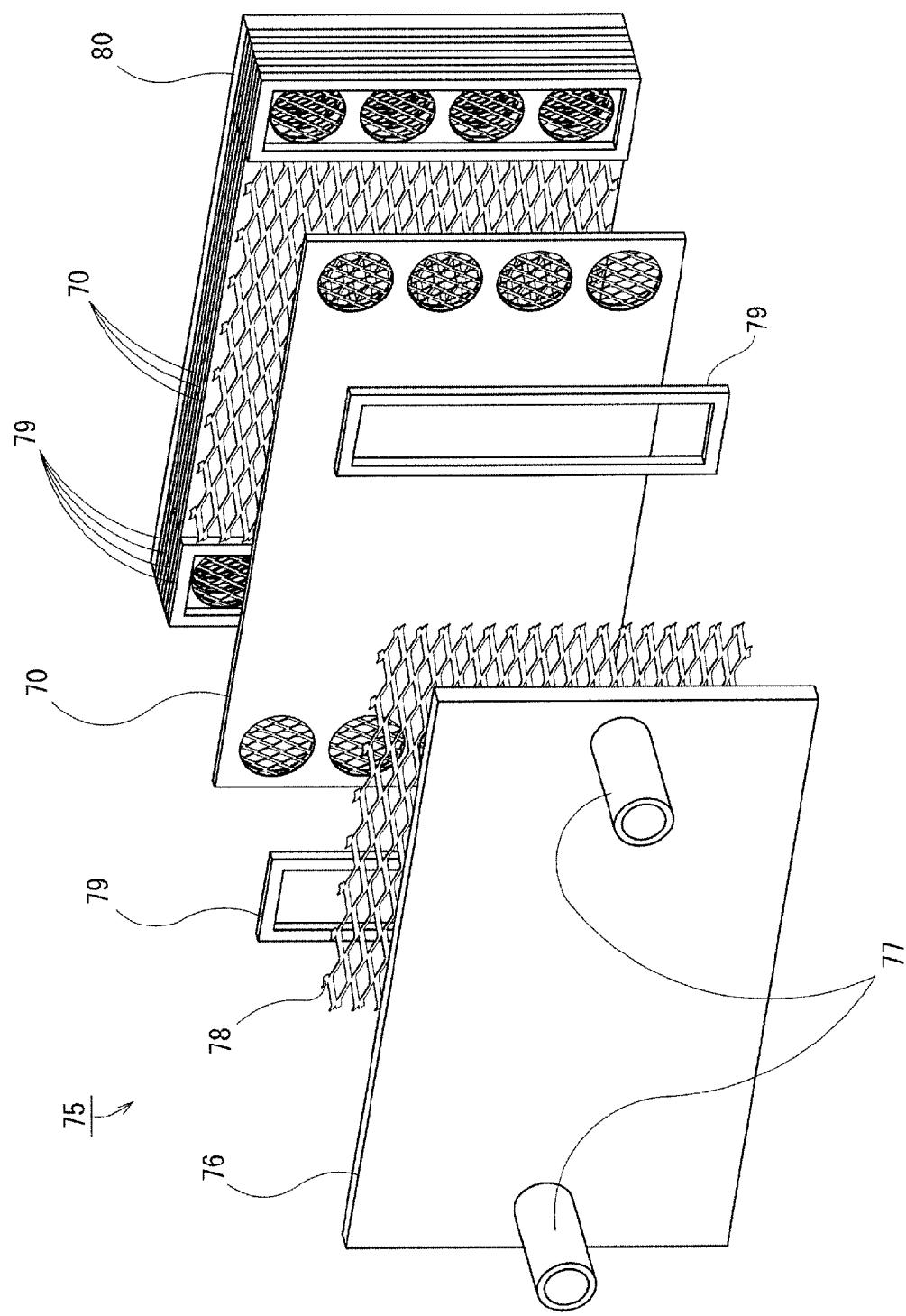
FIG. 19 is an exploded perspective view showing a condenser (heat exchanger) according to the embodiment.

FIG. 19 shows a condenser used for a lithium bromide system absorption refrigerating machine according to the embodiment comprising the above-described plate type heat exchanger tube 70. The condenser 75 is constructed by longitudinally laminating a large number of plate type heat exchanger tubes 70. On both the front and rear ends of these laminated plate type heat exchanger tubes 70, end plates 76 and 80 are disposed. To the one end plate 76, cooling water lines 77 and 77 are connected. Between the end plate 76 or 80 and the plate type heat exchanger tube 70, and between the plate type exchanger tube 70 and the plate type heat exchanger tube 70, respectively, an expanded metal 78 and communicating tubes 79 are disposed. The communicating tubes 79 are disposed in a manner that surround a plurality of fluid inflow ports 72 and a plurality of fluid outflow ports 73, respectively. To the communicating tubes 79 and 79, the cooling water lines 77 and 77 are connected.

Figure 20:
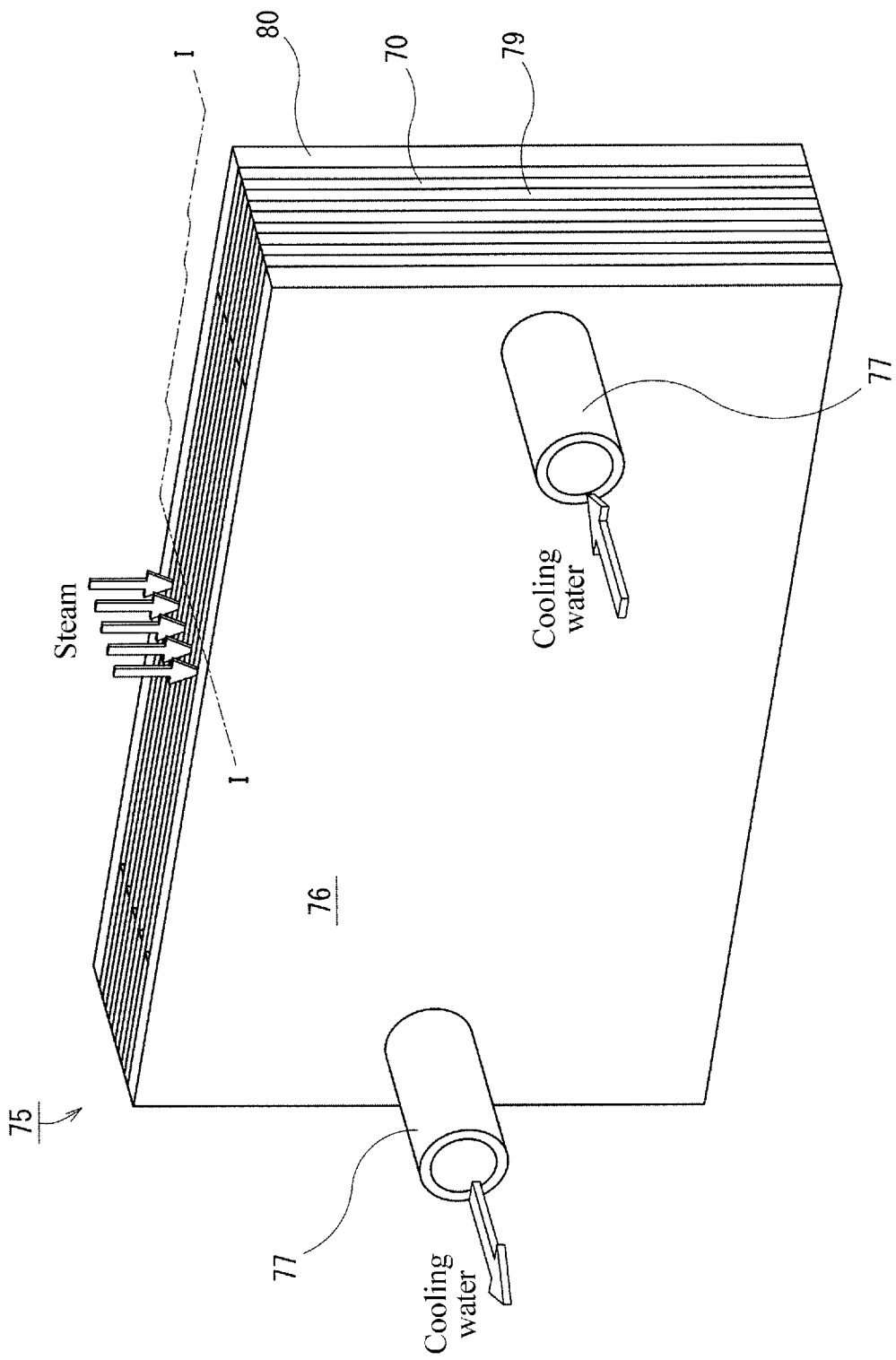
FIG. 20 is a perspective view showing the condenser (heat exchanger) according to the embodiment.
Figure 21:
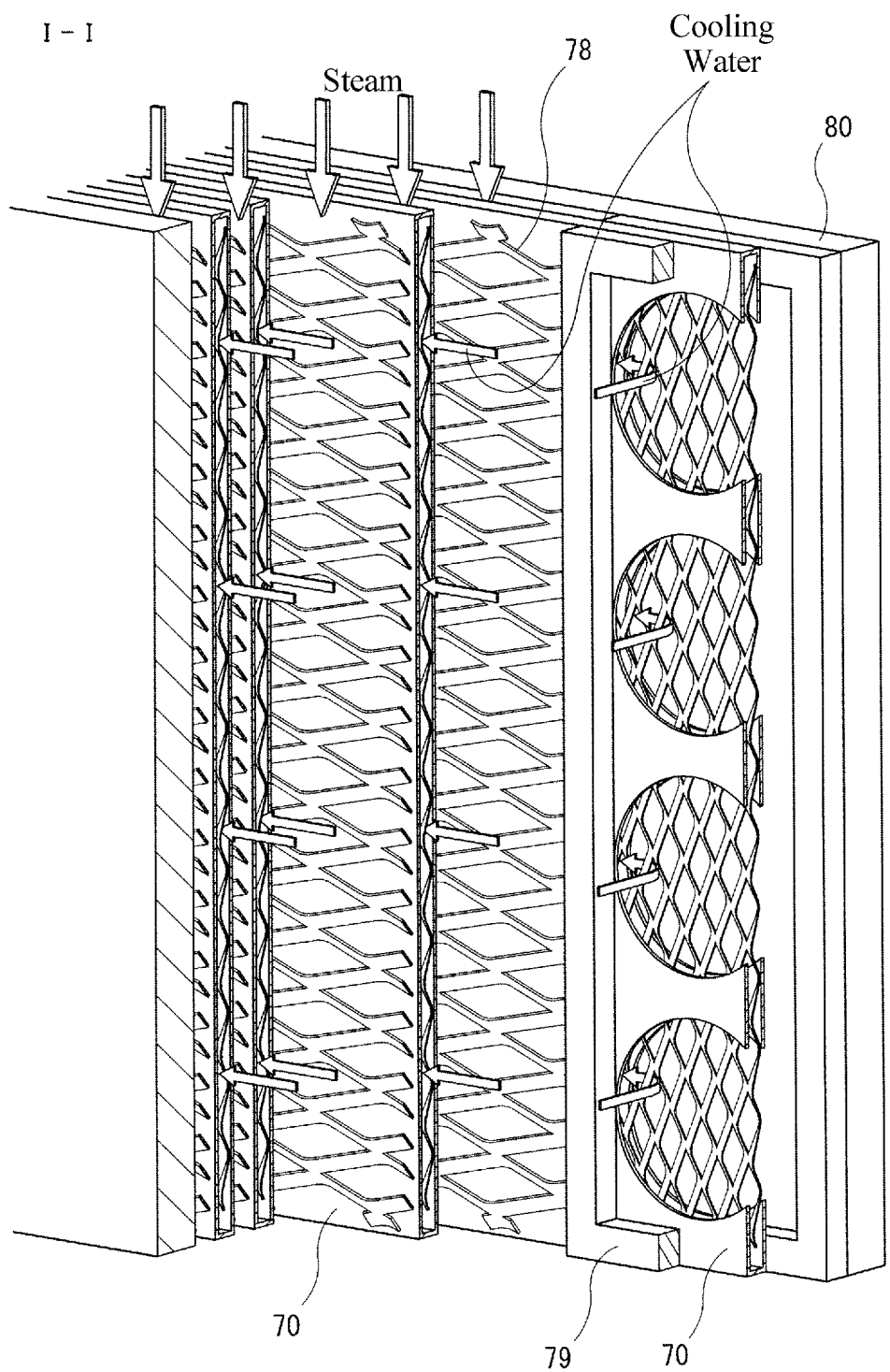
FIG. 21 is a partially cross-sectional perspective view showing the condenser (heat exchanger) according to the embodiment.

FIG. 20 shows the condenser 75 in a state wherein a large number of plate type heat exchanger tubes 70 and the end plates 76 and 80 are assembled. Within the condenser 75, steam and cooling water flow as shown in FIG. 21, so that the steam is very efficiently cooled and condensed.

Thus, by arranging the expanded metal 78 in the channel wherein steam flows along the outside heat-transfer surface 71 of the plate type heat exchanger tube 70, local fluid flows of a steam flow stir the inner part of a condensate film flowing down on the heat-transfer surface 71 and causes forced convection heat transfer within the condensate film, leading to greatly improving the condensation heat transfer coefficient.

An absorber used for the lithium bromide system absorption refrigerating machine can be also realized by having the same construction as the embodiment, wherein a liquid film of a lithium bromide solution (absorbing solution) is allowed to flow along the outside heat-transfer surface 71 of the plate type heat exchanger tube 70. With the turbulence of a temperature boundary layer and a density boundary layer within the absorbing solution film running down on the heat-transfer surface 71 increased by local fluid flows of a steam flow, the absorption and diffusion of steam into the absorbing solution film are promoted.

Figure 22:
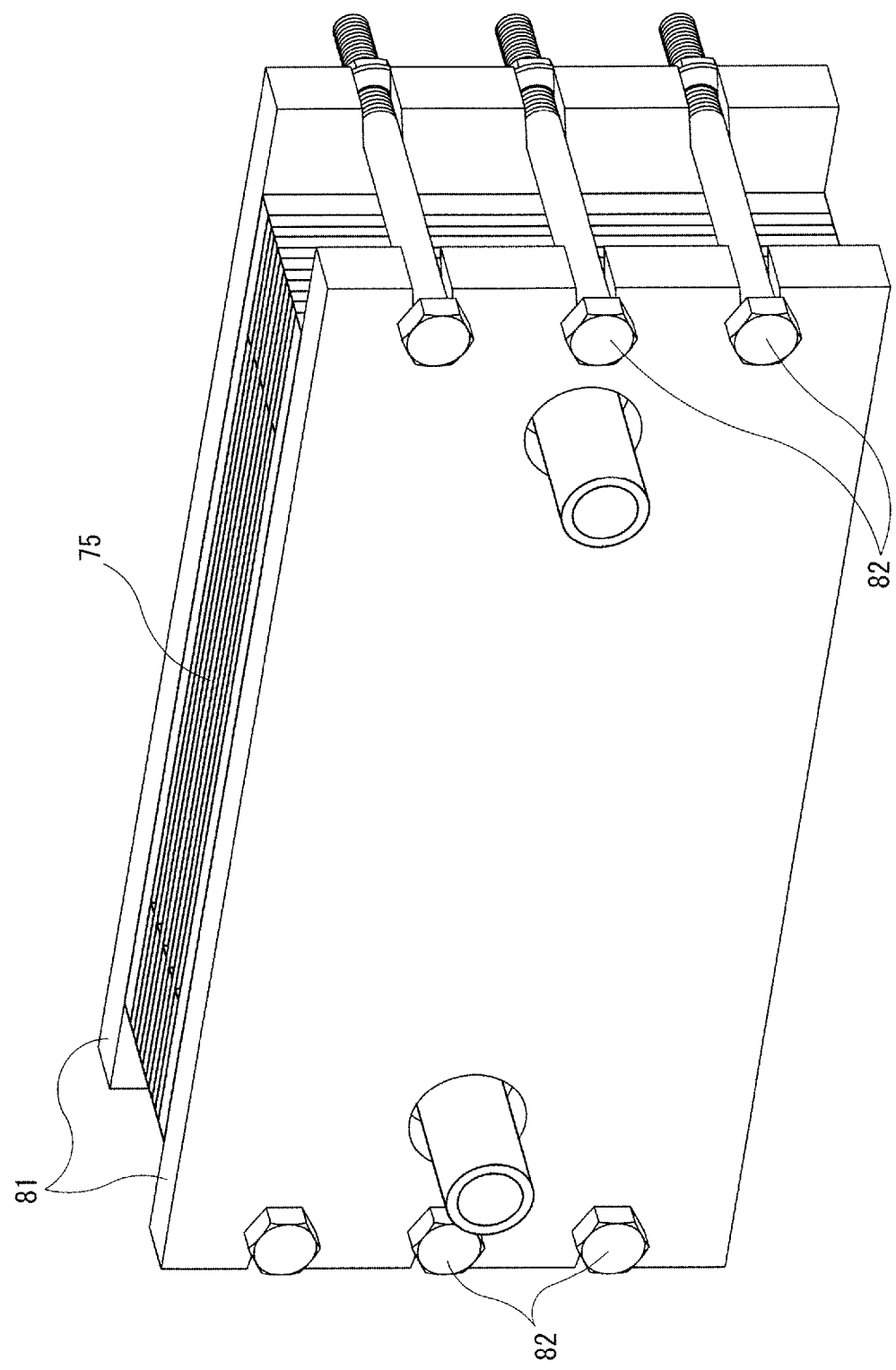
FIG. 22 is a perspective view showing a state wherein the condenser according to the embodiment is held within a shell.

Here, since the condenser and the absorber of the absorption refrigerating machine each are held in a high vacuum shell, they need be held in the shell in a manner shown in FIG. 22 in order to prevent the plate type heat exchanger tubes 70 from being broken by cooling water pressure. FIG. 22 shows the condenser 75 in a state of reinforced with pressuretight frames 81, wherein the condenser 75 is sandwiched between the pressuretight frames 81 using bolts 82 and fixed.

Figure 23:
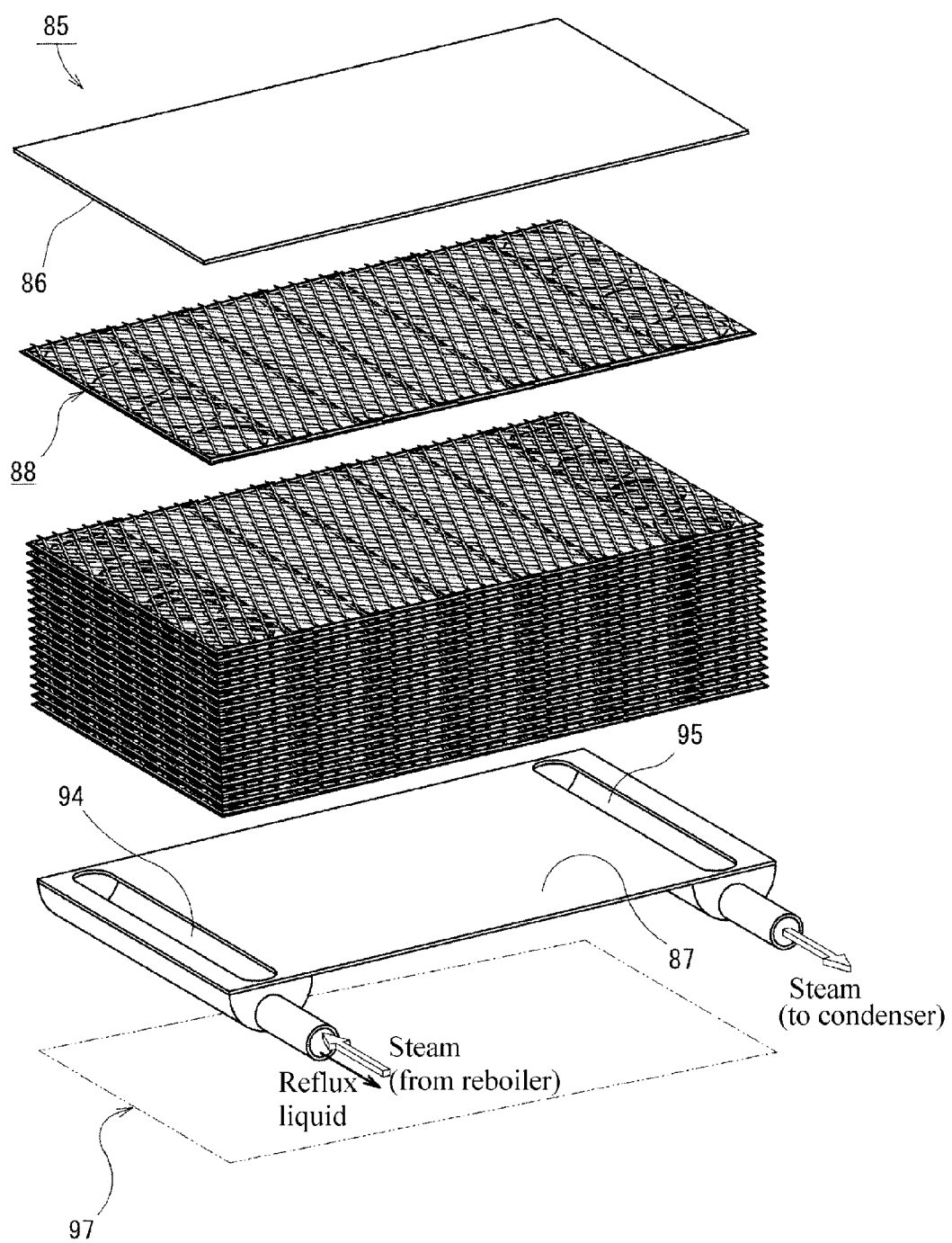
FIG. 23 is an exploded perspective view showing a distillation column according to the embodiment.
Figure 24:
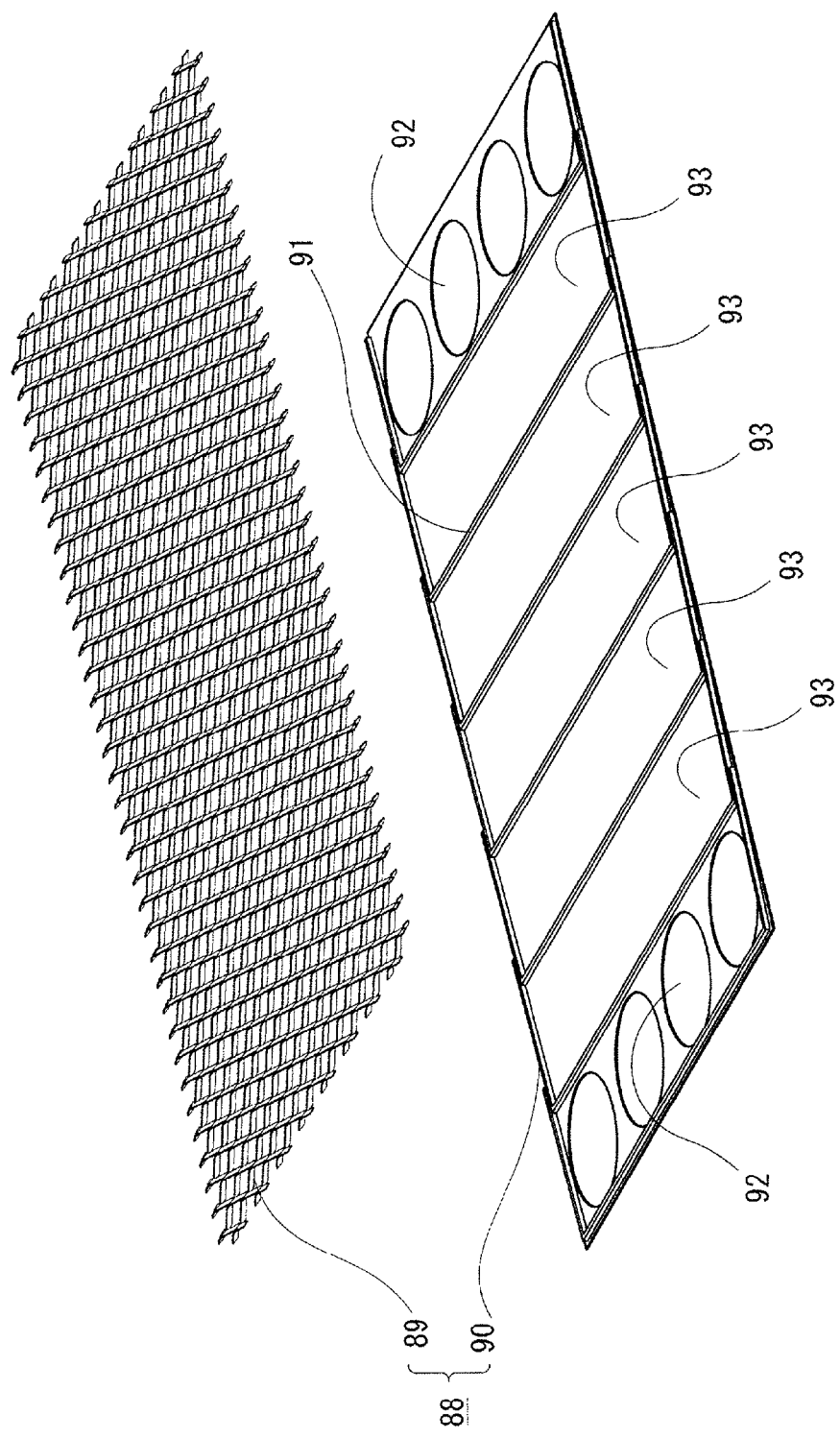
FIG. 24 is an exploded perspective view showing a shelf plate of the distillation column according to the embodiment.

FIG. 23 shows an exploded perspective view of a distillation column according to the embodiment. The distillation column 85 comprises a large number of shelf plates 88 vertically laminated between a top plate 86 and a bottom plate 87. The shelf plate 88 comprises an expanded metal 89 and a tray 90 as shown in FIG. 24. On the tray 90, banks 91 which divide the tray 90 into many blocks so as to form pools 93 are formed. In the vicinities of both end portions in the longitudinal direction of the tray 90, a plurality of openings 92 are formed. Through these openings 92, each shelf plate 88 is communicated to a steam supply port 94 and a steam discharge port 95 formed on the bottom plate 87. The bottom plate 87 is placed in such a manner that the steam discharge port 95 side is slightly higher than the steam supply port 94 side, compared with a horizontal plane 97 (higher by a small slope of one-in-several-tens to one-in-several-hundreds to the horizontal plane 97), and therefore, the steam supplied from the steam supply port 94 side slowly ascends toward the steam discharge port 95 side. By allowing the steam to slowly flow, it is possible to decrease the pressure loss to an extreme.

Figure 25:
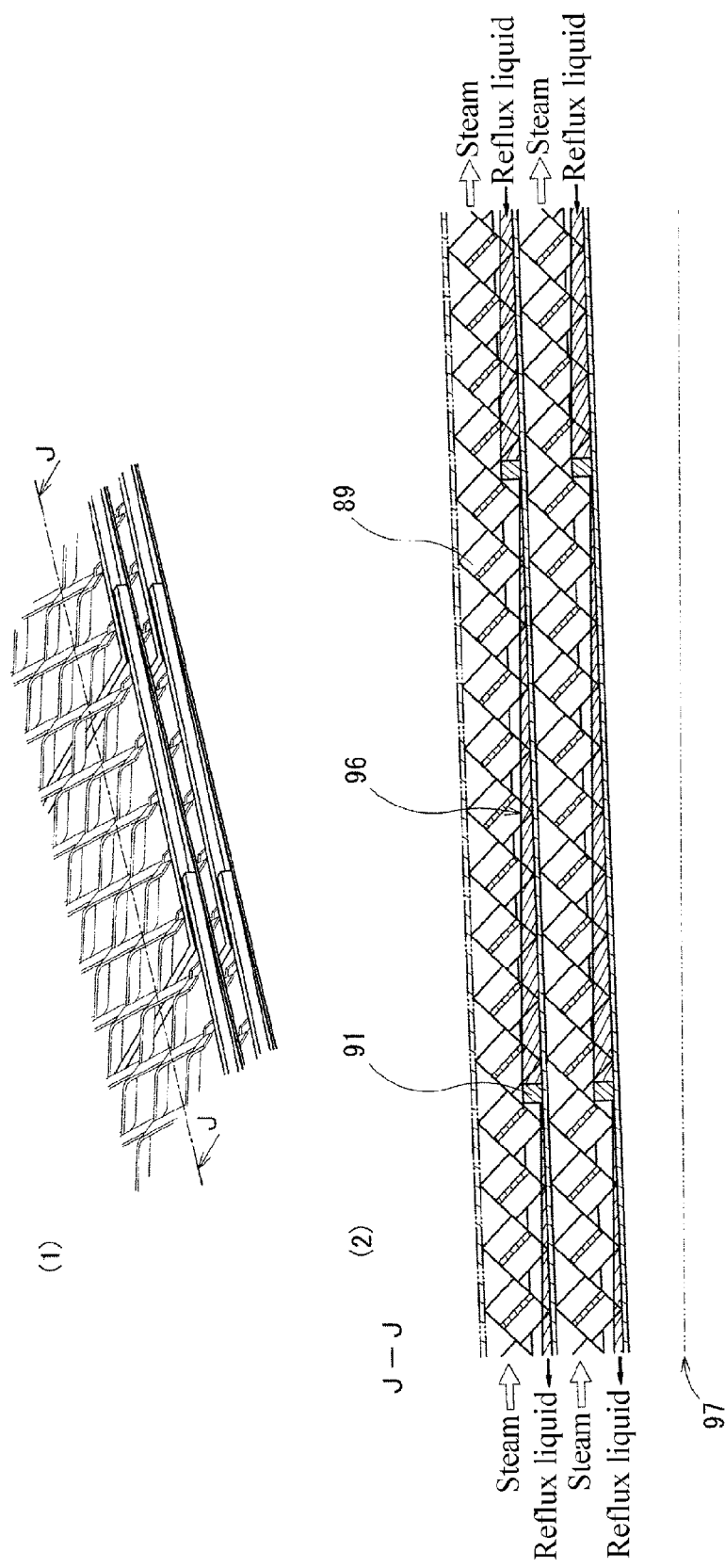
FIGS. 25(1) and 25(2) are a partially cross-sectional perspective view and a cross-sectional view showing two shelf plates of the distillation column according to the embodiment, respectively.

The height of the reflux liquid surface 96 of each pool 93 is controlled by the bank 91 as shown in FIG. 25. The height of the bank 91 is selected so as to allow the steam and a reflux liquid to sufficiently make contact with each other, with consideration given to the whole thickness D of the expanded metal 89. The vertical load onto the shelf plate 88 does not weigh upon the bank 91. The reflux liquid is supplied to the pool 93 located in the column top side highest portion of each shelf plate 88 by a distributor (not shown), and while being accumulated in each pool 93, the reflux liquid slowly flows down.

Through a local turbulent flow acceleration effect by the expanded metal 89, a density boundary layer in the vapor phase formed due to a decrease in high-boiling component in the vapor phase in the neighborhood of the gas-liquid interface becomes thin, and the diffusion resistance of the high-boiling component in the vapor phase to the gas-liquid interface becomes small, leading to promoting mass transfer.

In another embodiment, which is not shown, the distillation column 85 shown in FIG. 23 can be also used as a deodorizing apparatus. When used as a deodorizing apparatus, with an adsorption liquid which easily adsorbs odor components in the gas phase in place of a reflux liquid, the deodorizing apparatus can very efficiently perform deodorizing.

In the above embodiment, as heat exchangers, a cooling apparatus for cooling heat-generating bodies such as semiconductor power modules, a condenser and an absorber in an absorption refrigerating machine were exemplified, but the condenser and the absorber according to the present invention are not limited to the condenser and the absorber in the absorption refrigerating machine There is no need to say that the present invention can be also applied to condensers and absorbers which are independent, other than those in the absorption refrigerating machine.

INDUSTRIAL APPLICABILITY

The present invention can be widely applied in the field of device industry including heat transfer and mass transfer such as the electronic device industry, the plant industry and every kind of device industry.

DESCRIPTION OF REFERENCE SIGNS

11: Channel plane
12: Channel
13, 13A, 13B: Expanded metal
14: Fluid flow
15: Boundary layer
16: Local fluid flow
17: Expanded metal mesh
18: Strand
19: Bond
20: Fixed channel portion
21: Fluid inlet line
22: Fluid outlet line
23: Bolt insertion hole
24, 25: Header
26: Fluid supply port
27: Fluid outflow port
28: Fixed expanded metal
29: Heat-transfer plate
30: Variable channel portion
31: Fluid inlet line
32: Fluid outlet line
33: Bolt insertion hole
34, 35: Header
36: Fluid supply port
37: Fluid outflow port
38: Rectangular channel plane
39: Variable expanded metal
40: Variable spacer
41: Variable gasket
42: Fixed gasket
43: Bolt
44: Nut
45: Chilled water channel
46: Hot water channel
50: Hot water reservoir
51: Pump
52, 54: Valve
53: Cooling device
55, 56, 57, 58: Thermocouple
59: Cooling apparatus
60: Heat-generating body
61: Radiation plate
62: O ring
63: Expanded metal
64: Cooling water inlet line
65: Cooling water outlet line
66: Fluid supply port
67: Fluid outflow port
68: Cooling unit
69: Cooling channel
70: plate type heat exchanger tube
71: Heat-transfer surface
72: Fluid inflow port
73: Fluid outflow port
75: Condenser
76, 80: End plate
77: Cooling water line
78: Expanded metal
79: Communicating tube
81: Pressuretight frame
82: Bolt
85: Distillation column
86: Top plate
87: Bottom plate
88: Shelf plate
89: Expanded metal
90: Tray
91: Bank
92: Opening
93: Pool
94: Steam supply port
95: Steam discharge port
96: Reflux liquid surface
97: Horizontal plane
LW: Long way of mesh
SW: Short way of mesh
T: Thickness
W: Width
D: Whole thickness

The invention claimed is:

1. A method for improving fluid flow characteristics, comprising:
   forming an expanded metal by push-cutting slits in a staggered arrangement in a steel plate and stretching the steel plate so as to form a metal mesh;
   providing the expanded metal in a channel formed by two planar members placed face-to-face, the expanded metal being disposed in the channel in such a manner such that a long way of the expanded metal mesh crosses the flow direction of the fluid at right angles; and
   allowing local fluid flows guided by the expanded metal to act on various boundary layers formed between the two planar members and a fluid so as to improve the fluid flow characteristics concerning heat transfer and/or mass transfer through a local turbulent flow acceleration effect.

2. The method for improving fluid flow characteristics according to claim 1, wherein a length of a hypotenuse of an isosceles right triangle having two other sides with a length of a width W of the expanded metal is set to be half of the short way SW of the expanded metal mesh.

3. A heat exchanger, to which the method for improving fluid flow characteristics according to claim 1 is applied.

4. A distillation apparatus, to which the method for improving fluid flow characteristics according to claim 1 is applied.

5. A deodorizing apparatus, to which the method for improving fluid flow characteristics according to claim 1 is applied.

6. An expanded metal used for the method for improving fluid flow characteristics according to claim 2, wherein the length of the hypotenuse of an isosceles right triangle having the other two sides with a length of the width W is set to be half of the short way SW of the expanded metal mesh.

* * * * *